(12) United States Patent
Miyawaki

(10) Patent No.: US 11,118,074 B2
(45) Date of Patent: Sep. 14, 2021

(54) DAMPING-IMPARTING AGENT AND RESIN COMPOSITION FOR DAMPING MATERIAL

(71) Applicant: Nippon Shokubai Co., Ltd., Osaka (JP)

(72) Inventor: Yukihiro Miyawaki, Osaka (JP)

(73) Assignee: Nippon Shokubai Co., Ltd., Osaka (JP)

( * ) Notice: Subject to any disclaimer, the term of this patent is extended or adjusted under 35 U.S.C. 154(b) by 57 days.

(21) Appl. No.: 15/562,354

(22) PCT Filed: Mar. 30, 2016

(86) PCT No.: PCT/JP2016/060317
§ 371 (c)(1),
(2) Date: Sep. 27, 2017

(87) PCT Pub. No.: WO2016/159047
PCT Pub. Date: Oct. 6, 2016

(65) Prior Publication Data
US 2018/0355193 A1    Dec. 13, 2018

(30) Foreign Application Priority Data

Mar. 31, 2015  (JP) .............................. JP2015-072883
Sep. 1, 2015  (JP) .............................. JP2015-172131
Sep. 1, 2015  (JP) .............................. JP2015-172132

(51) Int. Cl.
| | | |
|---|---|---|
| *C09D 7/63* | (2018.01) | |
| *C08J 9/18* | (2006.01) | |
| *C08K 5/42* | (2006.01) | |
| *C09D 7/40* | (2018.01) | |
| *C09D 5/02* | (2006.01) | |
| *C09D 171/02* | (2006.01) | |
| *C09K 3/00* | (2006.01) | |
| *F16F 15/02* | (2006.01) | |
| *C09D 167/02* | (2006.01) | |
| *C09D 133/00* | (2006.01) | |
| *C09D 135/00* | (2006.01) | |
| *C08F 2/26* | (2006.01) | |
| *C08L 33/06* | (2006.01) | |
| *C09D 201/02* | (2006.01) | |
| *C07C 309/17* | (2006.01) | |
| *C07C 309/18* | (2006.01) | |
| *C09D 133/10* | (2006.01) | |
| *F16F 1/36* | (2006.01) | |
| *F16F 1/37* | (2006.01) | |
| *B60R 13/08* | (2006.01) | |
| *E04B 1/82* | (2006.01) | |
| *E04B 1/74* | (2006.01) | |
| *G10K 11/162* | (2006.01) | |

(52) U.S. Cl.
CPC .............. *C09D 7/63* (2018.01); *C07C 309/17* (2013.01); *C07C 309/18* (2013.01); *C08F 2/26* (2013.01); *C08J 9/18* (2013.01); *C08K 5/42* (2013.01); *C08L 33/06* (2013.01); *C09D 5/022* (2013.01); *C09D 5/024* (2013.01); *C09D 7/40* (2018.01); *C09D 133/00* (2013.01); *C09D 133/10* (2013.01); *C09D 135/00* (2013.01); *C09D 167/02* (2013.01); *C09D 171/02* (2013.01); *C09D 201/02* (2013.01); *C09K 3/00* (2013.01); *F16F 1/3605* (2013.01); *F16F 1/37* (2013.01); *F16F 15/02* (2013.01); *B60R 13/08* (2013.01); *C08J 2203/22* (2013.01); *C08J 2333/10* (2013.01); *E04B 1/82* (2013.01); *E04B 2001/742* (2013.01); *F16F 2224/0225* (2013.01); *G10K 11/162* (2013.01)

(58) Field of Classification Search
CPC ....... C07C 309/17; C07C 309/18; C08F 2/26; C08J 2203/22; C08J 2333/10; C08J 9/18; C08K 5/42; C08L 33/06; C09D 133/00; C09D 133/10; C09D 135/00; C09D 167/02; C09D 171/02; C09D 201/02; C09D 5/022; C09D 5/024; C09D 7/40; C09D 7/63; C09K 3/00; F16F 2224/0225; F16F 1/3605; F16F 1/37; F16F 15/02; B60R 13/08; E04B 1/82; E04B 2001/742; G10K 11/162

See application file for complete search history.

(56) References Cited

U.S. PATENT DOCUMENTS

| | | | |
|---|---|---|---|
| 3,329,640 A | 7/1967 | Scotti et al. | |
| 3,947,400 A * | 3/1976 | Burkhard | C08F 2/24 524/747 |
| 4,148,746 A * | 4/1979 | Klemmensen | C08F 220/04 166/275 |
| 4,250,050 A * | 2/1981 | Asbeck | C07C 309/00 560/151 |
| 5,356,968 A * | 10/1994 | Rupaner | C08F 2/26 524/157 |
| 2007/0191535 A1 | 8/2007 | Kasai et al. | |
| 2008/0245989 A1 | 10/2008 | Miyawaki et al. | |

FOREIGN PATENT DOCUMENTS

| | | |
|---|---|---|
| CN | 101668784 | 3/2010 |
| EP | 1 652 883 | 5/2006 |

(Continued)

*Primary Examiner* — Irina S Zemel
(74) *Attorney, Agent, or Firm* — Hamre, Schumann, Mueller & Larson, P.C.

(57) ABSTRACT

The present invention aims to provide a coating material which has high mechanical stability and is capable of providing a coat which has excellent appearance and exhibits excellent damping properties in a wide temperature range. The present invention relates to a damping-imparting agent including a compound having a sulfosuccinic acid (salt) structure. The present invention also relates to a resin composition for damping materials, including an emulsion prepared by polymerizing a monomer component, the composition further including a component having a sulfosuccinic acid (salt) structure.

12 Claims, No Drawings

(56) References Cited

FOREIGN PATENT DOCUMENTS

| | | |
|---|---|---|
| EP | 1 930 390 | 6/2008 |
| JP | 2006-206677 | 8/2006 |
| JP | 2007-085385 | 4/2007 |
| JP | 4550703 B | 9/2010 |
| JP | 2010-275547 | 12/2010 |
| JP | 2012-207103 | 10/2012 |
| JP | 5159628 B | 3/2013 |
| JP | 2013-199531 | 10/2013 |
| JP | 5660779 B | 1/2015 |
| JP | 2017-048363 | 3/2017 |
| JP | 2017-048364 | 3/2017 |
| JP | 6461312 B | 1/2019 |
| WO | 2005/010095 | 2/2005 |
| WO | 2007/023821 | 3/2007 |
| WO | 2008/135403 | 11/2008 |

* cited by examiner

DAMPING-IMPARTING AGENT AND RESIN COMPOSITION FOR DAMPING MATERIAL

TECHNICAL FIELD

The present invention relates to a damping-imparting agent and a resin composition for damping materials. More specifically, the present invention relates to a damping-imparting agent, a resin composition for damping materials, a coating material containing the resin composition for damping materials, and a coat obtainable from the coating material, which are suitable for a variety of structures requiring damping properties.

BACKGROUND ART

Damping materials are used to prevent vibration and noise of a variety of structures to insure sustained quietude, and are widely used for, for example, underfloor spaces of automobile interior, and for railway vehicles, ships, aircraft, electric devices, buildings, and construction machinery. Conventional damping materials are plate- or sheet-like molded products made from materials having vibration absorbing performance and sound absorbing performance. As alternatives to such molded products, coating materials which can form coats to achieve effects of absorbing vibration and sound have been proposed. Coating materials including an emulsion prepared by emulsion polymerizing a monomer component have been proposed (see, for example, Patent Literatures 1 to 6). Furthermore, a coating material including an emulsion prepared by emulsion polymerizing a monomer component using a reactive emulsifier has been proposed (see, for example, Patent Literature 7).

CITATION LIST

Patent Literature

Patent Literature 1: JP 2012-207103 A
Patent Literature 2: WO 2007/023821
Patent Literature 3: JP 2010-275547 A
Patent Literature 4: JP 4550703 B
Patent Literature 5: JP 5159628 B
Patent Literature 6: JP 5660779 B
Patent Literature 7: JP 2013-199531 A

SUMMARY OF INVENTION

Technical Problem

Although a variety of coating materials have been proposed as described above, coating materials capable of providing coats which have excellent appearance and exhibit excellent damping properties in a wide temperature range still have not been produced yet.

The present invention has been made in view of the state of the art described above, and aims to provide a coating material which has high mechanical stability and is capable of providing a coat which has excellent appearance and exhibits excellent damping properties in a wide temperature range.

Solution to Problem

The present inventor examined materials which have high mechanical stability and are capable of providing coats which have excellent appearance and exhibit excellent damping properties in a wide temperature range, and reached a damping-imparting agent and a resin composition for damping materials, each of which contains a compound having a sulfosuccinic acid (salt) structure. The present inventor has found that such a damping-imparting agent and resin composition for damping materials can provide a coating material with high mechanical stability, and this coating material can provide a coat which has excellent appearance and exhibits remarkably excellent damping properties in a wide temperature range. Thus, the present inventor solved the above problems, thereby completing the present invention.

That is, the present invention relates to a damping-imparting agent containing a compound having a sulfosuccinic acid (salt) structure.

The present invention also relates to a resin composition for damping materials containing an emulsion prepared by polymerizing a monomer component, and the composition further contains a component having a sulfosuccinic acid (salt) structure.

The present invention is described in more detail below.

Any combination of two or more of the following preferred embodiments according to the present invention is also a preferred embodiment according to the present invention.

<Damping-Imparting Agent of the Present Invention>

The damping-imparting agent of the present invention contains a compound having a sulfosuccinic acid (salt) structure.

The present invention also relates to a method for using a compound having a sulfosuccinic acid (salt) structure, the method including mixing a compound having a sulfosuccinic acid (salt) structure as a damping-imparting agent and an emulsion prepared by polymerizing a monomer component.

The damping-imparting agent of the present invention can suitably provide a coat which has excellent appearance and exhibits remarkably excellent damping properties in a wide temperature range.

The reason why the damping-imparting agent of the present invention provides a coat with excellent appearance is presumed as follows. Conventional coating materials for damping materials contain a pigment such as calcium carbonate, a thickener, a dispersant, and a foaming agent such as a thermally expandable encapsulated foaming agent, and volatile components such as water in the emulsion are evaporated by heat-drying (baking) the coating materials. At this time, if a certain amount of a foaming agent is not added, a blister is formed in the coat. This is presumably because volatile components evaporate through the coating surface and a dried membrane is formed before volatile components in the coat completely evaporate. This dried membrane blocks evaporation passages for the volatile components in the coat, and the vapor of the volatile components left in the coat raise the dried membrane. The foaming agent thermally expands to form evaporation passages for volatile components, and through which volatile components are easily drained. Thereby, the formation of a blister is prevented.

The damping-imparting agent of the present invention containing a compound having a sulfosuccinic acid (salt) structure can provide a coat with good appearance and less blisters, even if the amount of a thermally expandable encapsulated foaming agent in the coating material is reduced or set to zero. The reason why a coat with good appearance is obtained is presumed as follows: the compound having a sulfosuccinic acid (salt) structure or a constituent unit derived from the compound, which constitutes a polymer in an emulsion, has emulsifying function and thermal foaming function, which causes fine foaming, for example, due to boiling, from the early stage of drying. Thus, drainage of moisture is maintained even under heating.

The damping-imparting agent of the present invention is preferably an emulsifier. The damping-imparting agent of the present invention which is an emulsifier may be an emulsifier used in emulsion polymerization or may be an agent added to a polymer prepared by a method other than emulsion polymerization to emulsify the polymer. In both cases, the compound having a sulfosuccinic acid (salt) structure contains a hydrophilic group (e.g., acid (salt) group) and a hydrophobic group (e.g., a site other than the acid (salt) group), and covers the surface of a polymer emulsion particle in the resin composition. The hydrophilic group of the component is oriented toward a solvent such as an aqueous solvent (the side opposite to the emulsion particle), and the hydrophobic group of the component is oriented toward the emulsion particle. Here, the phrase "compound covers the surface of a polymer emulsion particle" may include the case in which the compound does not completely cover the surface. For example, the emulsion particle may be partly exposed.

In particular, in order to sufficiently achieve the effects of the present invention, the damping-imparting agent of the present invention is preferably an emulsifier used in emulsion polymerization. When the damping-imparting agent of the present invention is an emulsifier used in emulsion polymerization for preparing an emulsion, the compound having a sulfosuccinic acid (salt) structure may be present as a compound different from the polymer that forms the emulsion, or may be present as a constituent unit of the polymer that forms the emulsion. Preferably, the compound is present as a compound different from the polymer that forms the emulsion. The compound having a sulfosuccinic acid (salt) structure is easily available and less costly, and is therefore advantageously used to prepare the damping-imparting agent of the present invention.

(Compound Having a Sulfosuccinic Acid (Salt) Structure)

The sulfosuccinic acid (salt) structure refers to a structure in which a sulfonic acid (salt) group is bonded to at least one of carbon atoms of —C—C— in the structure represented by —CO—C—C—COOR (wherein R represents a hydrogen atom, an alkyl group, a metal salt, an ammonium salt, or an organic amine salt).

The alkyl group for R is preferably a C1-C20 alkyl group, more preferably a C1-C15 alkyl group, still more preferably a C5-C10 alkyl group, particularly preferably, for example, a 2-ethylhexyl group. Examples of a metal atom of the metal salt for R include monovalent metal atoms such as alkali metal atoms (e.g., lithium, sodium, potassium); divalent metal atoms such as calcium and magnesium; and trivalent metal atoms such as aluminum and iron. Examples of the organic amine salt for R include alkanolamine salts such as an ethanolamine salt, a diethanolamine salt, and a triethanolamine salt; and a triethylamine salt.

R is preferably a hydrogen atom, an alkyl group, or a metal atom, more preferably an alkyl group or a metal atom, still more preferably a metal atom. The metal atom is still more preferably any of the above-described monovalent metal atoms, particularly preferably sodium.

The sulfonic acid (salt) group means a sulfonic acid group and/or a sulfonate group. Examples of the sulfonate group include metal salts, ammonium salts, and organic amine salts of a sulfonic acid group, and mixtures of these salts.

Examples of the metal atoms of the metal salts and the organic amine salts include those described above.

In order to provide a more sufficiently functional coat, the sulfonic acid (salt) group is more preferably a sulfonic acid group, a sodium sulfonate group, a magnesium sulfonate group, or a calcium sulfonate group; still more preferably a sodium sulfonate group, a magnesium sulfonate group, or a calcium sulfonate group; particularly preferably a sodium sulfonate group.

The sulfosuccinic acid (salt) structure further contains a hydrogen atom and/or a monovalent substituent other than a hydrogen atom bonded thereto. The compound having a sulfosuccinic acid (salt) structure may have a reactive unsaturated carbon-carbon bond and may become a constituent unit of the polymer in an emulsion by polymerization. Examples of the compound having a sulfosuccinic acid (salt) structure, which contains a reactive unsaturated carbon-carbon bond, include ELEMINOL JS-20 (trade name, produced by Sanyo Chemical Industries, Ltd.). However, in order to provide a coat with better appearance, the compound having a sulfosuccinic acid (salt) structure preferably has no reactive unsaturated carbon-carbon bond. In other words, the compound having a sulfosuccinic acid (salt) structure is preferably a non-reactive emulsifier for preparing an emulsion. The non-reactive emulsifier, which has no reactive unsaturated carbon-carbon bond, does not react in emulsion polymerization and does not constitute part of the polymer that forms the emulsion, and is present as a compound different from the polymer even after emulsion polymerization. When a compound having no reactive unsaturated carbon-carbon bond is used as the compound having a sulfosuccinic acid (salt) structure, the resin composition for damping materials of the present invention contains the compound having a sulfosuccinic acid (salt) structure rather than the constituent unit of the polymer that forms the emulsion. Thus, the effects of the present invention are remarkably exhibited to provide a coat with good appearance.

Examples of the substituent include a hydrocarbon group, an amino group, an alkoxy group, an alkylamino group, an alkoxysulfonyl group, a sulfoalkyl group, an aminoalkyl group, a carboxyl group, a polyalkylene oxide chain-containing group, and an alkenyloxy group. For example, the compound having a sulfosuccinic acid (salt) structure preferably has a hydrocarbon group. The number of carbon atoms of the hydrocarbon group is preferably 8 or more, more preferably 12 or more.

The compound having a sulfosuccinic acid (salt) structure preferably further has a polyalkylene oxide chain-containing group. The polyalkylene oxide chain-containing group may be a group consisting only of a polyalkylene oxide chain or a group containing a polyalkylene oxide chain and other structure site(s). Examples of the other structure site(s) include hydrocarbon groups such as saturated aliphatic hydrocarbon groups and aromatic hydrocarbon groups. The polyalkylene oxide chain-containing group is preferably a group consisting only of a polyalkylene oxide chain or a group in which a hydrogen atom or a hydrocarbon group is bonded to an oxygen atom at an end of the polyalkylene oxide chain. For example, preferably, the compound having a sulfosuccinic acid (salt) structure has a polyalkylene oxide chain-containing group and a hydrocarbon group having 8 or more carbon atoms, more preferably a hydrocarbon group having 12 or more carbon atoms, bonded to an end of the polyalkylene oxide chain-containing group.

In the compound having a sulfosuccinic acid (salt) structure, the average number of moles of oxyalkylene groups added constituting the polyalkylene oxide chain is preferably 3 or more, more preferably 4 or more, still more preferably 5 or more. The average number of moles added means an average of the number of moles of the oxyalkylene groups added per mol of the polyalkylene oxide chain of the compound having a sulfosuccinic acid (salt) structure.

The compound having a sulfosuccinic acid (salt) structure and having no reactive unsaturated carbon-carbon bond is preferably represented, for example, by the following formula (1):

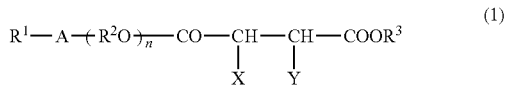

(1)

wherein $R^1$ represents a hydrogen atom or a C1-C30 monovalent alkyl group; -A- represents —O— or —NH—; $R^2$ represents a C1-C30 alkylene group; the average number n of moles added is 0 to 200; X and Y are the same as or different from each other and each represent a hydrogen atom or a sulfonic acid (salt) group, at least one of X and Y representing a sulfonic acid (salt) group; and $R^3$ represents a hydrogen atom, an alkyl group, a metal salt, an ammonium salt, or an organic amine salt.

$R^1$ preferably represents a C1-C30 monovalent alkyl group. The number of carbon atoms of $R^1$ is preferably 4 or more, more preferably 8 or more, still more preferably 12 or more. The number of carbon atoms of $R^1$ is preferably 25 or less, more preferably 20 or less.

The monovalent alkyl group is preferably a primary alkyl group or a secondary alkyl group.

In terms of improving the damping properties and the mechanical stability in a balanced manner, -A- preferably represents —NH—.

$R^2$s preferably mainly include a C2-C4 alkylene group such as an ethylene group, a propylene group, or a butylene group, more preferably an ethylene group.

The term "mainly" herein means, when the $(R^2O)_n$ site includes two or more different oxyalkylene groups, an oxyalkylene group(s) mainly contained preferably account(s) for 50 to 100 mol % of the total number of $R^2$s. The $(R^2O)_n$ site more preferably consists only of ethylene groups.

It is a preferred embodiment of the damping-imparting agent of the present invention that the average number n of moles added is 3 to 200. In terms of enhancing the function of the compound having a sulfosuccinic acid (salt) structure as an emulsifier to improve the damping properties, the average number n of moles added is more preferably 4 or more, still more preferably 5 or more, further more preferably 6 or more, particularly preferably 7 or more. The average number n of moles added is more preferably 100 or less, still more preferably 50 or less, further more preferably 20 or less, particularly preferably 10 or less. It is a preferred embodiment of the damping-imparting agent of the present invention that -A-represents —NH— and the average number n of moles added is 0.

X and Y are the same as or different from each other and each represent a hydrogen atom or a sulfonic acid (salt) group, and at least one of X and Y represents a sulfonic acid (salt) group. Preferably, either one of X and Y represents a sulfonic acid (salt) group, and the other represents a hydrogen atom. The preferred sulfonic acid (salt) group is as described above.

$R^3$ represents a hydrogen atom, an alkyl group, a metal salt, an ammonium salt, or an organic amine salt. $R^3$ is more preferably an alkyl group or a metal salt, still more preferably a metal salt. Examples of a metal atom of the metal salt include alkali metal atoms such as lithium, sodium, and potassium. Sodium is particularly preferred. Examples of the alkyl group and the organic amine salt represented by $R^3$ are the same as those described above.

It is a preferred embodiment of the damping-imparting agent of the present invention that the compound having a sulfosuccinic acid (salt) structure and having no reactive unsaturated carbon-carbon bond is represented, for example, by the following formula (2):

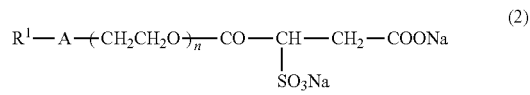

(2)

wherein $R^1$, -A-, and the average number n of moles added are the same as those described above for the formula (1).

The compound having a sulfosuccinic acid (salt) structure can be obtained, for example, by reaction of sulfosuccinic acid with a compound containing a substituent by a conventionally known method. When the substituent is a polyalkylene oxide chain-containing group, for example, the polyalkylene oxide chain-containing group can be introduced into the sulfosuccinic acid (salt) structure by reaction of an alkylene oxide such as ethylene oxide or a polyalkylene oxide chain-containing compound with a carboxylic acid group of the sulfosuccinic acid. The compound having a sulfosuccinic acid (salt) structure may be a commercial product or a product prepared by adding an aqueous solvent to a commercial product so that the solids concentration is appropriately adjusted.

The damping-imparting agent of the present invention may contain, for example, a conventionally known emulsifier such as an anionic surfactant described below other than the compound having a sulfosuccinic acid (salt) structure. The compound having a sulfosuccinic acid (salt) structure preferably accounts for 25% by mass or more, more preferably 50% by mass or more, still more preferably 60% by mass or more, further preferably 70% by mass or more, further more preferably 80% by mass or more, particularly preferably 90% by mass or more, most preferably 100% by mass of 100% by mass of the damping-imparting agent.

The damping-imparting agent of the present invention only has to provide a damping increase rate of higher than 0%, which is determined by the method described below. In particular, the damping increase rate determined by the method described below is preferably 5% or higher.

The damping increase rate is calculated by a method including the steps of:

(1) forming a coat by applying a coating material to a cold rolling steel plate (trade name, SPCC, produced by Nippon Testpanel Co., Ltd.) so as to have a thickness of 2 mm, by pre-drying the coating material at 80° C. for 30 minutes, and by drying the coating material at 150° C. for 30 minutes, the coating material containing an emulsion prepared by polymerizing a monomer component, the damping-imparting agent in such an amount that the amount of the compound having a sulfosuccinic acid (salt) structure is 3.0% by mass, calcium carbonate in an amount of $2.8×10^2$% by mass based on 100% by mass of the whole monomer component used as a material of the emulsion, and no thermally expandable encapsulated foaming agent;

(2) forming a coat in the same manner as in the step (1), except that the amount of the compound having a sulfosuccinic acid (salt) structure contained is 1.5% by mass; and (3) measuring loss coefficients of the coats formed in the steps (1) and (2) at 20° C., 30° C., 40° C., 50° C., and 60° C. using a loss coefficient measurement system produced by Ono Sokki Co., Ltd. by a cantilever method, and for each coat, summing the loss coefficients to determine the total loss coefficient; and (4) calculating the damping increase rate using the following expression:

Damping increase rate (%)={(a−b)/b}×100(%)

wherein a is the total loss coefficient of the coat formed in the step (1), and b is the total loss coefficient of the coat formed in the step (2).

The above-described amount $2.8 \times 10^2$% by mass of calcium carbonate only has to fall within the range of 275% by mass or more and less than 285% by mass. The amount of the calcium carbonate in the step (1) may be different from the amount of the calcium carbonate in the step (2) as long as each of these amounts falls within this range.

Examples of the thermally expandable encapsulated foaming agent include commercial products such as F-30 (trade name, produced by Matsumoto Yushi-Seiyaku Co., Ltd.).

The damping increase rate determined by the method described above is more preferably 6% or higher, still more preferably 7% or higher, most preferably 8% or higher.

<Resin Composition for Damping Materials of the Present Invention>

The resin composition for damping materials of the present invention contains an emulsion prepared by polymerizing a monomer component, and further contains a component having a sulfosuccinic acid (salt) structure.

The phrase "the resin composition for damping materials of the present invention contains a component having a sulfosuccinic acid (salt) structure" means that the emulsion is prepared through emulsion polymerization and the component is introduced into the composition by the use of the component as an emulsifier in emulsion polymerization for preparing the emulsion, by addition of to the component to the emulsion which is prepared by emulsion polymerization using another emulsifier, or by the use of part of the component as an emulsifier in emulsion polymerization and addition of the rest to the resulting emulsion; or that a polymer is prepared by a method other than emulsion polymerization and the component is introduced into the composition by the action of the composition as an emulsifier on the polymer to form an emulsion. In particular, in order to sufficiently achieve the effects of the present invention, the component having a sulfosuccinic acid (salt) structure is preferably an emulsifier, that is, it is preferred that the emulsion is prepared through emulsion polymerization and the component is introduced into the composition by the use of the component as an emulsifier in emulsion polymerization for preparing the emulsion or by the use of part of the component as an emulsifier in emulsion polymerization and addition of the rest to the resulting emulsion; or that a polymer is prepared by a method other than emulsion polymerization and the component is introduced into the composition by the action of the composition as an emulsifier on the polymer to form an emulsion. It is more preferred that the emulsion is prepared through emulsion polymerization and the component is introduced into the composition by the use of the component as an emulsifier in emulsion polymerization for preparing the emulsion. When the component is used as an emulsifier in emulsion polymerization, the component may be a usual emulsifier (a compound different from the polymer that forms the emulsion), or may be present as an emulsifier and a constituent unit of the polymer that forms the emulsion. Preferably, the component is present as a compound different from the polymer that forms the emulsion. The component having a sulfosuccinic acid (salt) structure herein may be the above-described compound having a sulfosuccinic acid (salt) structure or may become a constituent unit derived from the compound in the polymer that forms the emulsion by emulsion polymerization, and is preferably the compound having a sulfosuccinic acid (salt) structure. Further, part of the component having a sulfosuccinic acid (salt) structure is a compound having a sulfosuccinic acid (salt) structure, and the rest of the component is present as a constituent unit derived from the compound in the polymer that forms the emulsion.

As described above, in the resin composition for damping materials of the present invention, the component having a sulfosuccinic acid (salt) structure is preferably an emulsifier. The phrase "the component having a sulfosuccinic acid (salt) structure is an emulsifier" specifically means that the component contains a hydrophilic group (e.g., acid (salt) group) and a hydrophobic group (e.g., a site other than the acid (salt) group), and covers the surface of an emulsion particle. The hydrophilic group of the component is oriented toward a solvent such as an aqueous solvent (the side opposite to the emulsion particle), and the hydrophobic group of the component is oriented toward the emulsion particle. Here, the phrase "component covers the surface of an emulsion particle" includes the case in which the component does not completely cover the surface. For example, the emulsion particle may be partly exposed.

The resin composition for damping materials of the present invention can provide a coating material with high mechanical stability capable of suitably forming a coat which has excellent appearance and exhibits remarkably excellent damping properties in a wide temperature range.

The "resin composition for damping materials" herein is also referred to as "damping material". In other words, the present invention relates to a damping material containing an emulsion prepared by polymerizing a monomer component. The damping material may also be a damping material containing a component having a sulfosuccinic acid (salt) structure.

The resin composition for damping materials of the present invention may contain an anionic surfactant other than the component having a sulfosuccinic acid (salt) structure. The component having a sulfosuccinic acid (salt) structure preferably accounts for 25% by mass or more of 100% by mass of the anionic surfactant in the composition. In terms of achieving more remarkable effects of the present invention, the component more preferably accounts for 50% by mass or more, still more preferably 60% by mass or more. In particular, in terms of providing a coat with excellent appearance, the component further preferably accounts for 70% by mass or more, further more preferably 80% by mass or more, particularly preferably 90% by mass or more, most preferably 100% by mass. The anionic surfactant in the composition means all the agents serving as an anionic surfactant in the composition, regardless of the intended use of the agents. That is, the anionic surfactant in the composition may have additional functions as long as it functions as an anionic surfactant. Examples of the intended use include the use as an emulsifier (e.g., emulsifier used in emulsion polymerization), a dispersant, a wet penetrant, or a foaming agent.

When the anionic surfactant is used as an emulsifier in emulsion polymerization, similarly to the component having a sulfosuccinic acid (salt) structure, the anionic surfactant may be a usual emulsifier (a compound different from the polymer that forms the emulsion), or may be present as an emulsifier and a constituent unit of the polymer that forms the emulsion.

The anionic surfactant other than the component having a sulfosuccinic acid (salt) structure is disclosed, for example, in JP 5030780 B and JP 2014-52024 A. Examples of the anionic surfactant include polyoxyalkylene alkyl ether sulfates such as LEVENOL WX (trade name, sodium polyoxyethylene alkyl ether sulfate, produced by Kao Corporation); polyoxyalkylene polycyclic phenyl ether sulfates such as NEWCOL 707SF (trade name, polyoxyethylene polycyclic phenyl ether sulfate, produced by Nippon Nyukazai Co., Ltd.); alkyl diphenyl ether disulfonates; reactive anionic emulsifiers such as alkenyl succinate-type anionic surfactants; and other anionic emulsifiers commonly used (e.g., sodium lauryl sulfate). One or two or more of these anionic surfactants may be used.

The resin composition for damping materials of the present invention may further contain an emulsifier other than anionic surfactants. The emulsifier other than anionic surfactants may be any of the emulsifiers disclosed in JP 2014-52024 A, for example.

The resin composition for damping materials of the present invention preferably contains the component having a sulfosuccinic acid (salt) structure in an amount of 0.1% to 20% by mass based on 100% by mass of the whole monomer component used as a material of the emulsion. In order to achieve the effects of the present invention such as mechanical stability, the amount of the component having a sulfosuccinic acid (salt) structure is more preferably 0.5% by mass or more, still more preferably 1% by mass or more, further more preferably 2% by mass or more, particularly preferably 3% by mass or more. The amount of the component having a sulfosuccinic acid (salt) structure is more preferably 15% by mass or less, still more preferably 10% by mass or less, further more preferably 8% by mass or less, particularly preferably 6% by mass or less.

Herein, the whole monomer component used as a material of the emulsion in the resin composition for damping materials of the present invention means monomer units constituting the polymer that forms the emulsion and monomers and oligomers derived from a monomer used as a material of the emulsion, excluding the component having a sulfosuccinic acid (salt) structure. The amount of the component having a sulfosuccinic acid (salt) structure corresponds to the total amount of the compound having a sulfosuccinic acid (salt) structure and the constituent unit derived from the compound in the polymer that forms the emulsion. In other words, the amount of the component having a sulfosuccinic acid (salt) structure corresponds to the total amount of all the compounds having a sulfosuccinic acid (salt) structure used to obtain the resin composition for damping materials of the present invention.

The amount of the component having a sulfosuccinic acid (salt) structure in the resin composition for damping materials of the present invention can be calculated as including the components present as constituent units in the polymer that forms the emulsion by adding up the amounts of all the compounds having a sulfosuccinic acid (salt) structure used as the material. Such an amount of the component having a sulfosuccinic acid (salt) structure can also be determined by adding up the amount of the compound having a sulfosuccinic acid (salt) structure in the resin composition for damping materials of the present invention and the amount of the constituent unit derived from the compound having a sulfosuccinic acid (salt) structure in the polymer that forms the emulsion.

Further, it is a preferred embodiment of the resin composition for damping materials of the present invention that the preferred amount of the compound having a sulfosuccinic acid (salt) structure (a compound different from the polymer that forms the emulsion) in the resin composition for damping materials of the present invention falls within the above-described preferred range of the amount of the component having a sulfosuccinic acid (salt) structure. In this preferred embodiment, the resin composition for damping materials of the present invention may contain the component having a sulfosuccinic acid (salt) structure as a constituent unit of the polymer that forms the emulsion in addition to the compound having a sulfosuccinic acid (salt) structure.

The amount of the compound having a sulfosuccinic acid (salt) structure in the resin composition for damping materials of the present invention can be determined by high-performance liquid chromatography on a component extracted from a coat dried by heating. In the case of using the compound having a sulfosuccinic acid (salt) structure having a reactive unsaturated carbon-carbon bond in polymerization, the compound having a sulfosuccinic acid (salt) structure, present not as a constituent unit of the polymer that forms the emulsion, can be analyzed.

(Emulsion Prepared by Polymerizing Monomer Component)

The resin composition for damping materials of the present invention contains an emulsion prepared by polymerizing a monomer component. In particular, the resin composition for damping materials of the present invention preferably contains an emulsion prepared by emulsion polymerizing a monomer component. The emulsion according to the present invention preferably has a weight average molecular weight of 20,000 to 800,000.

In order to exhibit the damping properties, it is preferred to convert the energy due to vibration applied to the polymer into frictional thermal energy, and the polymer needs to be movable when vibration is applied thereto. The emulsion according to the present invention having such a weight average molecular weight can sufficiently move when vibration is applied thereto, and thus can exhibit excellent damping properties. The weight average molecular weight of the emulsion according to the present invention is more preferably 30,000 or more, still more preferably 35,000 or more, further more preferably 50,000 or more, particularly preferably 90,000 or more. The weight average molecular weight is more preferably 500,000 or less, still more preferably 420,000 or less, further more preferably 400,000 or less, particularly preferably 270,000 or less. The weight average molecular weight of the emulsion herein refers to the weight average molecular weight of the polymer that forms the emulsion. The weight average molecular weight (Mw) can be measured using GPC under the conditions disclosed in the below described examples.

The emulsion may be any of a variety of emulsions miscible with the compound having a sulfosuccinic acid (salt) structure. For example, the emulsion preferably contains a polymer that includes a carboxylic acid (salt) group-containing monomer unit. The carboxylic acid (salt) group means a carboxylic acid group and/or a carboxylate group.

Preferred examples of a salt of the carboxylate group-containing monomer unit include metal salts, ammonium salts, and organic amine salts. Preferred examples of a metal atom of the metal salts include monovalent metal atoms including alkali metal atoms such as lithium, sodium, and potassium; divalent metal atoms such as calcium and magnesium; and trivalent metal atoms such as aluminum and iron. Preferred examples of the organic amine salts include alkanolamine salts such as an ethanolamine salt, a diethanolamine salt, and a triethanolamine salt; and a triethylamine salt.

The carboxylic acid (salt) group-containing monomer unit is preferably a constituent unit derived from a (meth)acrylic acid monomer. In other words, the emulsion preferably contains a (meth)acrylic polymer. The (meth)acrylic polymer refers to a polymer containing a constituent unit derived from a (meth)acrylic acid monomer.

For example, the monomer component for producing a (meth)acrylic polymer preferably includes a (meth)acrylic acid monomer and other copolymerizable unsaturated monomer(s). The (meth)acrylic acid monomer improves the dispersibility of an inorganic pigment and other components in the coating material containing the resin composition for damping materials of the present invention. Thereby, the resulting coat can have better functions. Furthermore, addition of other copolymerizable unsaturated monomer(s) enables easy adjustment of properties such as the acid value, Tg, and physical properties of the polymer.

The (meth)acrylic acid monomer contains at least one group of an acryloyl group, a methacryloyl group, and a group obtained by replacing a hydrogen atom of either of these groups with another atom or an atomic group, and a carboxyl group (—COOH group) or an acid anhydride group (—C(=O)—O—C(=O)— group) which has the carbonyl group of the at least one group. The (meth)acrylic acid monomer is preferably (meth)acrylic acid.

The (meth)acrylic polymer is preferably prepared by, for example, copolymerizing a monomer component composed of 0.1% to 5% by mass of the (meth)acrylic acid monomer and 95% to 99.9% by mass of other copolymerizable unsaturated monomer(s). The monomer component is more preferably composed of 0.3% by mass or more of the (meth)acrylic acid monomer and 99.7% by mass or less of other copolymerizable unsaturated monomer(s), still more preferably composed of 0.5% by mass or more of the (meth)acrylic acid monomer and 99.5% by mass or less of other copolymerizable unsaturated monomer(s), particularly preferably composed of 0.7% by mass or more of the (meth)acrylic acid monomer and 99.3% by mass or less of other copolymerizable unsaturated monomer(s). The monomer component is preferably composed of 5% by mass or less of the (meth)acrylic acid monomer and 95% by mass or more of other copolymerizable unsaturated monomer(s), more preferably composed of 4% by mass or less of the (meth)acrylic acid monomer and 96% by mass or more of other copolymerizable unsaturated monomer(s), still more preferably composed of 3% by mass or less of the (meth)acrylic acid monomer and 97% by mass or more of other copolymerizable unsaturated monomer(s). The monomer component with the above described composition can be stably copolymerized.

Examples of the other copolymerizable unsaturated monomer(s) include (meth)acrylic monomers other than the (meth)acrylic acid monomer, aromatic ring-containing unsaturated monomers, and other copolymerizable unsaturated monomers.

The (meth)acrylic monomers other than the (meth)acrylic acid monomer refer to monomers that contain an acryloyl group, a methacryloyl group, or a group obtained by replacing a hydrogen atom in either of these groups with another atom or an atomic group, and a carboxyl group in the form of an ester or a salt; or refer to derivatives of the monomers.

Examples of the (meth)acrylic monomers other than the (meth)acrylic acid monomer include methyl acrylate, methyl methacrylate, ethyl acrylate, ethyl methacrylate, propyl acrylate, propyl methacrylate, isopropyl acrylate, isopropyl methacrylate, butyl acrylate, butyl methacrylate, isobutyl acrylate, isobutyl methacrylate, tert-butyl acrylate, tert-butyl methacrylate, pentyl acrylate, pentyl methacrylate, isoamyl acrylate, isoamyl methacrylate, hexyl acrylate, hexyl methacrylate, cyclohexyl acrylate, cyclohexyl methacrylate, octyl acrylate, octyl methacrylate, isooctyl acrylate, isooctyl methacrylate, nonyl acrylate, nonyl methacrylate, isononyl acrylate, isononyl methacrylate, decyl acrylate, decyl methacrylate, dodecyl acrylate, dodecyl methacrylate, tridecyl acrylate, tridecyl methacrylate, hexadecyl acrylate, hexadecyl methacrylate, octadecyl acrylate, octadecyl methacrylate, 2-ethylhexyl acrylate, 2-ethylhexyl methacrylate, vinyl formate, vinyl acetate, vinyl propionate, 2-hydroxyethyl acrylate, 2-hydroxyethyl methacrylate, 2-hydroxypropyl acrylate, 2-hydroxypropyl methacrylate, diallyl phthalate, triallyl cyanurate, ethylene glycol diacrylate, ethylene glycol dimethacrylate, 1,4-butanediol diacrylate, 1,4-butanediol dimethacrylate, 1,6-hexanediol diacrylate, 1,6-hexanediol dimethacrylate, diethylene glycol diacrylate, diethylene glycol dimethacrylate, allyl acrylate, and allyl methacrylate; and salts or esterified products of (meth)acrylic acid monomers other than these listed above. One or two or more of these may be preferably used.

Preferred examples of the salts of the (meth)acrylic acid monomers include metal salts, ammonium salts, and organic amine salts. Examples of the metal salts and organic amine salts include those described as the salts of a carboxylate group-containing monomer unit.

The monomer component serving as the material of the (meth)acrylic polymer contains the (meth)acrylic monomer other than the (meth)acrylic acid monomer in an amount of preferably 20% by mass or more, more preferably 40% by mass or more, still more preferably 60% by mass or more based on 100% by mass of the whole monomer component used as a material of the emulsion. The monomer component serving as the material of the (meth)acrylic polymer contains the (meth)acrylic monomer other than the (meth)acrylic acid monomer in an amount of preferably 99.9% by mass or less, more preferably 99.5% by mass or less based on 100% by mass of the whole monomer component.

Examples of the aromatic ring-containing unsaturated monomers include divinylbenzene, styrene, α-methylstyrene, vinyl toluene, and ethyl vinyl benzene. Preferred is styrene. That is, it is also a preferred embodiment of the present invention that the (meth)acrylic polymer is a styrene (meth)acrylic polymer obtained from a monomer component containing styrene. Such an embodiment enables cost reduction and sufficient exhibition of the effects of the present invention.

When the monomer component serving as the material of the (meth)acrylic polymer contains the aromatic ring-containing unsaturated monomer, the amount thereof is preferably 1% by mass or more, more preferably 5% by mass or more, still more preferably 10% by mass or more, further more preferably 20% by mass or more, particularly preferably 40% by mass or more based on 100% by mass of the whole monomer component used as a material of the emulsion. Further, the monomer component contains the aromatic ring-containing unsaturated monomer in an amount of preferably 80% by mass or less, more preferably 70% by mass or less, still more preferably 60% by mass or less based on 100% by mass of the whole monomer component. The monomer component serving as the material of the (meth)acrylic polymer may not include the aromatic ring-containing unsaturated monomer.

Examples of the other copolymerizable unsaturated monomer(s) include polyfunctional unsaturated monomers such as acrylonitrile and trimethylolpropane diallyl ether.

Preferably, the resin composition for damping materials of the present invention contains an aqueous solvent, and the emulsion is dispersed in the aqueous solvent. The phrase "dispersed in the aqueous solvent" herein means that the emulsion is not dissolved but dispersed in the aqueous solvent. Herein, the aqueous solvent may contain an organic solvent as long as the aqueous solvent contains water.

The resin composition for damping materials of the present invention may contain one or two or more emulsions prepared by polymerizing a monomer component (hereinafter, also referred to as emulsions according to the present invention). When the resin composition for damping materials of the present invention contains two or more emulsions according to the present invention, the two or more emulsions according to the present invention may be in the form of a mixture obtained by mixing (blending) the two or more emulsions according to the present invention, or may be in the form of an emulsion composite of two or more polymer chains which is obtained by producing a product containing two or more polymer chains in a series of production steps (e.g., multistage polymerization). The product containing two or more emulsions according to the present invention may be obtained in a series of production steps by appropriately setting the production conditions such as conditions for dropwise addition of monomers. The composite of two or more polymer chains may have, for example, a core part and a shell part as described below. As the emulsions according to the present invention having a core part and a shell part, the emulsions according to the present invention may consist of two emulsions according to the present invention, and one emulsion forms a core part and the other forms a shell part, for example. Here, when the (meth)acrylic polymer is formed from a monomer component that contains a (meth)acrylic acid monomer, the (meth)acrylic acid monomer may be contained in either a core-forming monomer component or a shell-forming monomer component in emulsions, or may be contained in both the core-forming monomer component and the shell-forming monomer component, for example.

At least one of the emulsions according to the present invention forming the emulsions may be in the form of a composite of two or more polymer chains.

When the emulsion according to the present invention is in the form of a composite of two or more polymer chains, the composite may have a homogeneous structure in which one polymer chain and the other are completely mixed with each other and therefore cannot be distinguished from each other, or a structure in which one polymer chain and the other are not completely mixed with each other and inhomogeneously formed (e.g., core-shell composite structure or microdomain structure). Among these structures, for example, the core-shell composite structure is preferred for the production of a stable emulsion with sufficient performance as an emulsion.

The emulsion with a core-shell composite structure exhibits excellent damping properties in a wide practical temperature range, and particularly in a higher temperature range, also exhibits excellent damping properties than resin compositions for damping materials with other structures. Thus, the emulsion with a core-shell composite structure can exhibit excellent damping properties in a wide practical temperature range from room temperature to a high temperature range.

In the core-shell composite structure, a core part surface is preferably covered with a shell part. In this case, the core part surface is preferably completely covered with the shell part, but may not be completely covered therewith. For example, the core part surface may be covered in a mesh pattern or may be partly exposed.

The emulsion according to the present invention preferably has a glass transition temperature of $-20°$ C. to $40°$ C. Use of the emulsion according to the present invention having such a glass transition temperature can provide a coat capable of effectively exhibiting damping properties in the practical temperature range. The glass transition temperature of the emulsion according to the present invention is more preferably $-15°$ C. to $35°$ C., still more preferably $-10°$ C. to $30°$ C. The glass transition temperature of the emulsion herein refers to the glass transition temperature of the polymer that forms the emulsion.

The glass transition temperature (Tg) can be calculated by the method disclosed in the below described examples. When at least one of the emulsions according to the present invention is prepared by multistage polymerization (e.g., in the form of emulsion particles having a core part and a shell part), the glass transition temperature means Tg (total Tg) determined from the proportion of the monomers used in all the stages.

When at least one of the emulsions according to the present invention is in the form of a composite of two or more polymer chains, the glass transition temperature of one of the polymer chains (e.g., a polymer chain as a core part) is preferably $0°$ C. to $60°$ C., more preferably $10°$ C. to $50°$ C.

The glass transition temperature of the other polymer chain (e.g., a polymer chain as a shell part) is preferably $-30°$ C. to $30°$ C., more preferably $-20°$ C. to $20°$ C.

The difference in glass transition temperature between one polymer chain and the other polymer chain is preferably $5°$ C. to $60°$ C. By setting such a difference in glass transition temperature, the emulsion can impart excellent damping properties in a wide temperature range when used for damping materials. In particular, the damping properties can be further improved in a practical range of from $20°$ C. to $60°$ C. The difference in glass transition temperature is more preferably $10°$ C. to $50°$ C., still more preferably $20°$ C. to $40°$ C.

The emulsion particles in the emulsion according to the present invention preferably have an average particle size of 80 to 450 nm.

Use of the emulsion particles having an average particle size within the above range can achieve excellent damping properties as well as sufficient basic properties required for damping materials, such as coat appearance and coatability. The average particle size of the emulsion particles is more preferably 400 nm or smaller, still more preferably 350 nm or smaller. The average particle size is preferably 100 nm or greater.

The average particle size of the emulsion particles can be measured by the method disclosed in the below described examples.

In the emulsion, the solids preferably account for 40% to 80% by mass, more preferably 50% to 70% by mass of the entire emulsion.

The solids herein refer to components excluding solvents such as an aqueous solvent contained in the emulsion.

The pH of the emulsion is not particularly limited, and is preferably 2 to 10, more preferably 3 to 9.5, still more preferably 7 to 9. The pH of the emulsion can be adjusted by adding ammonia water, a water-soluble amine, an alkali hydroxide aqueous solution, or the like, to the resin.

The pH herein can be measured by the method disclosed in the below described examples.

The viscosity of the emulsion is not particularly limited, and is preferably 1 to 10,000 mPa·s, more preferably 5 to 4,000 mPa·s, still more preferably 10 to 2,000 mPa·s, furthermore preferably 30 to 1,000 mPa·s, particularly preferably 80 to 500 mPa·s.

The viscosity herein can be measured under the conditions disclosed in the below described examples.

The emulsion (polymer) may be produced by any method. For example, the emulsion can be produced by the same method as the production method of emulsion for damping materials disclosed in JP 2011-231184 A. The emulsion may be produced by a method other than emulsion polymerization. For example, the emulsion may be formed by allowing the component having a sulfosuccinic acid (salt) structure to act as an emulsifier on a polymer prepared by suspension polymerization.

The solids of the emulsion according to the present invention preferably account for 20% by mass or more, more preferably 30% by mass or more, still more preferably 40% by mass or more, particularly preferably 50% by mass or more of 100% by mass of the solids of the resin composition for damping materials of the present invention. The solids preferably accounts for 99% by mass or less, more preferably 97% by mass or less, still more preferably 95% by mass or less, particularly preferably 93% by mass or less, most preferably 91% by mass or less of 100% by mass of the solids of the resin composition for damping materials of the present invention.

The solids refer to components excluding solvents such as an aqueous solvent.

The resin composition for damping materials of the present invention may be an emulsion prepared by emulsion polymerizing a monomer emulsion as a material containing the entire compound having a sulfosuccinic acid (salt) structure and a monomer component, or may be a product produced by emulsion polymerizing a monomer emulsion as a material containing part of the compound having a sulfosuccinic acid (salt) structure and a monomer component to prepare an emulsion, and adding the rest of the compound having a sulfosuccinic acid (salt) structure to the resulting emulsion. Thus, when the monomer emulsion as a material containing at least part of the compound having a sulfosuccinic acid (salt) structure and a monomer component is emulsion polymerized, the at least part of the component having a sulfosuccinic acid (salt) structure is contained as an emulsifier that forms the emulsion. In this case, the at least part of the component having a sulfosuccinic acid (salt) structure may be present as a usual emulsifier (a compound different from the polymer), or may be present as an emulsifier and a constituent unit constituting part of the polymer.

As described above, the resin composition for damping materials of the present invention may be prepared by emulsion polymerizing a monomer component not containing a compound having a sulfosuccinic acid (salt) structure to prepare an emulsion or polymerizing a monomer component by a method other than emulsion polymerization to prepare a polymer, and adding a compound having a sulfosuccinic acid (salt) structure as an emulsifier to the resulting emulsion or polymer. In particular, the resin composition for damping materials of the present invention is preferably produced by polymerizing a monomer component by a method other than emulsion polymerization to prepare a polymer, and adding a compound having a sulfosuccinic acid (salt) structure as an emulsifier to the resulting polymer.

The present invention also relates to a method for producing a resin composition for damping materials including emulsion polymerizing a monomer emulsion as a material containing a compound having a sulfosuccinic acid (salt) structure and a monomer component or including polymerizing a monomer component, as a material, by a method other than emulsion polymerization to prepare a polymer and adding a compound having a sulfosuccinic acid (salt) structure to the polymer. The polymerization temperature is not particularly limited, and is preferably 0° C. to 100° C., for example. The polymerization time is not particularly limited, and is preferably 1 to 15 hours, for example.

The resin composition for damping materials of the present invention may contain other component(s) as long as the resin composition contains the component having a sulfosuccinic acid (salt) structure according to the present invention and the emulsion prepared by polymerizing a monomer component.

When the resin composition for damping materials of the present invention contains other component(s), the amount of the other component(s) is preferably 10% by mass or less, more preferably 5% by mass or less based on the entire resin composition. The other component(s) herein refer(s) to nonvolatile component(s) (solid(s)) left in a coat obtained by applying the resin composition for damping materials of the present invention and heat-drying the applied composition. The other component(s) does/do not include a volatile component such as an aqueous solvent.

As described above, the resin composition for damping materials of the present invention preferably contains a solvent such as an aqueous solvent. The solvent preferably accounts for 3% by mass or more, more preferably 10% by mass or more, still more preferably 20% by mass or more, particularly preferably 30% by mass or more of 100% by mass of the resin composition for damping materials of the present invention. The amount of the solvent is preferably 97% by mass or less, more preferably 90% by mass or less, still more preferably 80% by mass or less of 100% by mass of the resin composition for damping materials of the present invention.

The resin composition for damping materials of the present invention itself may be applied to form a damping film. Still, it is usually used to obtain the below described coating material of the present invention.

The present invention also relates to a method for using a resin composition for damping materials including supplying the resin composition for damping materials of the present invention as a material of a coating material for mixing with a pigment. The supplying is not particularly limited, and may be, for example, transfer to a person who intends to implement the mixing with a pigment.

In the method for using the resin composition for damping materials of the present invention, the coating material is suitable for transportation such as vehicles, railway vehicles, ships, and aircraft, electric devices, buildings, and construction machinery. For example, the coating material is preferably a coating material for vehicles.

<Coating Material of the Present Invention>

The present invention also relates to a coating material containing the resin composition for damping materials of the present invention and a pigment.

A preferred resin composition for damping materials contained in the coating material of the present invention is the same as the above described preferred resin composition for damping materials of the present invention.

The solids of the resin composition for damping materials preferably account for 1% by mass or more, more preferably 5% by mass or more, still more preferably 10% by mass or more of 100% by mass of the solids of the coating material of the present invention. Further, the solids of the resin composition for damping materials preferably account for 50% by mass or less, more preferably 40% by mass or less, still more preferably 30% by mass or less of 100% by mass of the solids of the coating material of the present invention.

The pigment may be, for example, one or two or more of inorganic colorants, organic colorants, antirust pigments, and fillers. Examples of the inorganic colorants include titanium oxide, carbon black, and colcothar. Examples of the organic colorants include dyes and natural colorants. Examples of the antirust pigments include metal phosphates, metal molybdates, and metal borates. Examples of the fillers include inorganic fillers such as calcium carbonate, kaolin, silica, talc, barium sulfate, alumina, iron oxide, glass powder, magnesium carbonate, aluminum hydroxide, diatomaceous earth, and clay; flaky inorganic fillers such as glass flakes and mica; and fibrous inorganic fillers such as metal oxide whiskers, glass fibers, and wollastonite. In particular, the pigment is preferably an inorganic pigment such as an inorganic colorant, an antirust pigment, or an inorganic filler, and calcium carbonate is more preferred.

The pigment preferably has an average particle size of 1 to 50 μm. The average particle size of the pigment can be measured with a laser diffraction particle size distribution analyzer, and is a value of the particle size at which the weight according to the particle size distribution reaches 50%.

The amount of the pigment is preferably 10 parts by mass or more, more preferably 200 parts by mass or more, still more preferably 300 parts by mass or more based on 100 parts by mass of the resin solids in the coating material of the present invention (whole monomer component used as a material of the emulsion).

The amount of the pigment is preferably 900 parts by mass or less, more preferably 800 parts by mass or less, still more preferably 500 parts by mass or less based on 100 parts by mass of the resin solids in the coating material of the present invention (whole monomer component used as a material of the emulsion).

The coating material of the present invention may further contain a dispersant.

Examples of the dispersant include inorganic dispersants such as sodium hexametaphosphate and sodium tripolyphosphate and organic dispersants such as polycarboxylic acid dispersants.

The amount of the dispersant, in terms of solids content, is preferably 0.1 to 8 parts by mass, more preferably 0.5 to 6 parts by mass, still more preferably 1 to 3 parts by mass based on 100 parts by mass of the resin solids in the coating material of the present invention.

The coating material of the present invention may further contain a thickener.

Examples of the thickener include polyvinyl alcohol, cellulose derivatives, and polycarboxylic acid resins.

The amount of the thickener is preferably 0.01 to 5 parts by mass, more preferably 0.1 to 4 parts by mass, still more preferably 0.3 to 2 parts by mass based on 100 parts by mass of the resin solids in the coating material of the present invention.

The coating material of the present invention may further contain a different component. Examples of the different component include foaming agents, solvents, gelling agents, defoaming agents, plasticizers, stabilizers, wetting agents, antiseptic agents, foaming inhibitors, antioxidants, mildewproofing agents, ultraviolet absorbers, and antistatic agents. One or two or more of these may be used.

The inorganic pigment, dispersant, thickener, and the different component can be mixed with the polymer emulsion according to the present invention and a cross-linking agent, for example, by means of a butterfly mixer, planetary mixer, spiral mixer, kneader, or dissolver.

Examples of the solvent include water and organic solvents such as ethylene glycol, butyl cellosolve, butyl carbitol, and butyl carbitol acetate. The amount of the solvent may be appropriately set to adjust the solids concentration of the coating material of the present invention.

Preparation of a coat from the coating material of the present invention, particularly preparation of a coat by heat-drying the coating material of the present invention enables simultaneous drying and foaming of the coating material, thereby forming a path for evaporation of a solvent such as water. As a result, a blister of the coat can be suppressed, and a coat with very good appearance can be obtained. Furthermore, since the component having a sulfosuccinic acid (salt) structure serves as a foaming agent, the amount of a commonly used expensive foaming agent (e.g., thermally expandable encapsulated foaming agent) can be reduced. For example, the amount of the thermally expandable encapsulated foaming agent is preferably reduced to 2% by mass or less, more preferably 1% by mass or less, most preferably 0% by mass based on 100% by mass of the whole monomer component used as a material of the emulsion.

Since the coating material of the present invention contains a component having a sulfosuccinic acid (salt) structure which serves as a foaming agent, the amount of the thermally expandable encapsulated foaming agent can be reduced to 2% by mass or less or further reduced. Thereby, deformation of the coat caused by an excessive amount of the foaming agent can be sufficiently prevented. Thus, the coating material can provide a coat with better appearance.

For example, in the coating material of the present invention, the amount of the thermally expandable encapsulated foaming agent is 2% by mass or less based on 100% by mass of the whole monomer component used as a material of the emulsion.

Accordingly, the coating material of the present invention can provide a coat with excellent appearance even if it has the above formulation, for example, an inexpensive formulation containing a large amount of a pigment such as calcium carbonate and a reduced amount of a thermally expandable encapsulated foaming agent. In addition, the coating material of the present invention having such a formulation imparts excellent damping properties.

The coating material of the present invention preferably has a total loss coefficient of 0.348 or higher, more preferably 0.374 or higher.

For example, it is a preferred embodiment of the coating material of the present invention that the amount of the pigment is 10% by mass or more and the amount of the thermally expandable encapsulated foaming agent is 2% by mass or less based on 100% by mass of the whole monomer component used as a material of the emulsion, and the total loss coefficient is 0.348 or higher.

The total loss coefficient can be determined by the method disclosed in the below described examples.

<Coating of the Present Invention and Method for Producing the Same>

The present invention also relates to a coat obtainable from the coating material of the present invention.

A preferred coating material used for the production of the coat of the present invention is the same as the above described preferred coating material of the present invention.

The present invention also relates to a coat obtainable by heating a coating material that contains an emulsion prepared by polymerizing a monomer component, a component having a sulfosuccinic acid (salt) structure, and a pigment to foam the coating material. The present invention also relates to a method for producing a coat, including heating a coating material that contains an emulsion prepared by polymerizing a monomer component, a component having a sulfosuccinic acid (salt) structure, and a pigment to foam the coating material, thereby producing a coat.

Preferred embodiments of the coat of the present invention are described below.

The coat of the present invention preferably has a thickness of 2 to 8 mm. Such a thickness is preferred in consideration of achievement of more sufficient damping properties, prevention of, for example, peeling or cracks of the coat, and formation of the good coat. The thickness of the coat is more preferably 2 to 6 mm, still more preferably 2 to 5 mm.

A base material on which the coat of the present invention is formed may be any material on which the coat can be formed, and may be, for example, a plastic material or a metal material such as a steel plate. In particular, formation of a coat on the surface of a steel plate is one preferred embodiment of the use of the damping coat of the present invention.

The coat of the present invention can be obtained by applying the coating material of the present invention by means of, for example, brush, spatula, air spray, airless spray, mortar gun, or texture gun.

The coat of the present invention is preferably obtained by foaming the coating material of the present invention applied to a base material by heat-drying. Here, in order to foam the coating material by heat-drying, the coating material is usually not mechanically foamed, for example, by stirring, before the heat-drying. The heat-drying is preferably performed such that the temperature of the coat obtained by applying the coating material to a base material preferably falls within the range of 40° C. to 200° C., more preferably 90° C. to 180° C., still more preferably 100° C. to 160° C. Before the heat-drying, the coat may be pre-dried at a lower temperature.

The coat is preferably heated at the temperature for 1 to 300 minutes, more preferably 2 to 250 minutes, particularly preferably 10 to 150 minutes.

The damping properties of the coat of the present invention can be evaluated by measuring the loss coefficient of the coat.

The loss coefficient is usually represented by η, and indicates the degree of attenuation of vibration applied to the coat. The higher the loss coefficient, the better the damping properties.

The loss coefficient can be measured by the method disclosed in the below described examples.

The coat of the present invention has excellent appearance and exhibits remarkably excellent damping properties in a wide temperature range, and the coating material for forming the coat has excellent mechanical stability. Therefore, the coat of the present invention is suitable for transportation such as vehicles, railway vehicles, ships, and aircraft, electric devices, buildings, and construction machinery.

Advantageous Effects of Invention

The damping-imparting agent of the present invention contains a compound having a sulfosuccinic acid (salt) structure, and therefore suitably provides a coat that has excellent appearance and exhibits remarkably excellent damping properties in a wide temperature range.

DESCRIPTION OF EMBODIMENTS

The following description is offered to demonstrate the present invention based on examples of the present invention. The embodiments should not be construed as limiting the present invention. Unless otherwise mentioned, the term "part(s)" means "part(s) by weight" and "%" means "% by mass".

The properties were evaluated as follows in the production examples.

<Average Particle Size>

The average particle size of emulsion particles was measured by dynamic light scattering using a particle size distribution analyzer (FPAR-1000, produced by Otsuka Electronics Co., Ltd.).

<Nonvolatile Content (N.V.)>

About 1 g of an emulsion obtained was weighed out and dried in a hot air dryer at 150° C. for one hour. The residue amount after drying was measured as the nonvolatile content and expressed as % by mass relative to the mass of the emulsion before drying.

<pH>

The pH at 25° C. was measured using a pH meter ("F-23" produced by Horiba, Ltd.).

<Viscosity>

The viscosity was measured at 25° C. and 20 rpm using a B-type rotary viscometer ("VISCOMETER TUB-10" produced by Toki Sangyo Co., Ltd.).

<Weight Average Molecular Weight>

The weight average molecular weight was measured by gel permeation chromatography (GPC) under the following conditions.

Measuring equipment: HLC-8120GPC (trade name, produced by Tosoh Corporation)
Molecular weight column: TSK-GEL GMHXL-L and TSK-GEL G5000HXL (both produced by Tosoh Corporation) connected in series
Eluent: Tetrahydrofuran (THF)
Calibration curve reference material: Polystyrene (produced by Tosoh Corporation)
Measuring method: A measurement object was dissolved in THF to a solids content of about 0.2% by mass, and the resulting solution was filtered through a filter. The filtrate was used as a measurement sample, and the molecular weight thereof was measured.

<Glass Transition Temperature (Tg) of Polymer>

The Tg of the polymer was calculated from the following formula (1) based on the proportion of the monomers used in the stages.

$$\frac{1}{Tg'} = \left[\frac{W_1'}{T_1} + \frac{W_2'}{T_2} + \ldots + \frac{W_n'}{T_n}\right] \quad (1)$$

In the formula, Tg' represents Tg (absolute temperature) of the polymer; $W_1'$, $W_2'$, ..., and $W_n'$ each represent the mass fraction of each monomer relative to the whole monomer component; and $T_1$, $T_2$, ..., and $T_n$ each represent the glass transition temperature (absolute temperature) of the homopolymer of each monomer.

The Tg determined from the proportion of the monomers in all the stages was expressed as "total Tg". The following shows the glass transition temperatures (Tg) of the homopolymers of the respective polymerizable monomer components which were used to calculate the Tg based on the formula (1).
Methyl methacrylate (MMA): 105° C.
Styrene (St): 100° C.
2-Ethylhexyl acrylate (2EHA): −70° C.
Butyl acrylate (BA): −56° C.
Acrylic acid (AA): 95° C.

The damping-imparting agents used in the following examples are described below. The damping-imparting agents described below also serve as an emulsifier.

A polyoxyethylene alkyl ether-sulfosuccinate-disodium salt is a compound represented by the following formula (i):

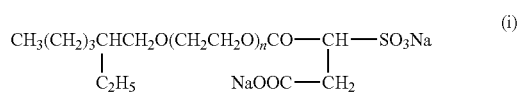

wherein n represents an average number of moles added. Herein, the compound in which n is 8 is also referred to as a compound (i)-<1>, and the compound in which n is 2 is also referred to as a compound (i)-<2>.

A dialkyl succinate sodium sulfonate is a compound represented by the following formula (ii):

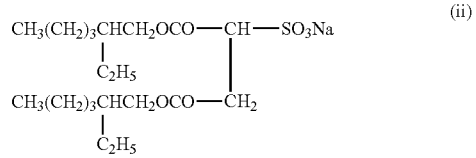

Herein, the compound is also referred to as a compound (ii).

A polyoxyethylene alkyl ether-sulfosuccinic acid half ester salt is a compound represented by the following formula (iii):

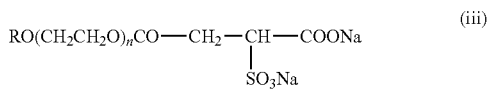

wherein R represents a C12-C14 secondary alkyl group; and n represents an average number of moles added. Herein, the compound in which n is 9 is also referred to as a compound (iii)-<1>, and the compound in which n is 3 is also referred to as a compound (iii)-<2>.

A N-alkyl monoamide disodium sulfosuccinate is a compound represented by the following formula (iv):

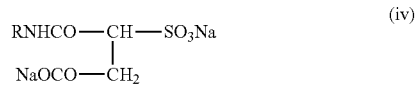

wherein R represents a C14-C20 alkyl group. Herein, this compound is also referred to as a compound (iv).

A sulfosuccinate-type reactive anionic surfactant is a compound represented by the following formula (v):

$$CH_2=CH-CH_2-OCO-CH(CH_2COOR)-SO_3Na \quad (v)$$

wherein R represents an alkyl group. Herein, this compound is also referred to as a compound (v).

The emulsifiers used in Comparative Examples are described below.
NEWCOL 707SF (trade name, polyoxyethylene polycyclic phenyl ether-sulfate, produced by Nippon Nyukazai Co., Ltd.)
LEVENOL WX (trade name, sodium polyoxyethylene alkyl ether sulfate, produced by Kao Corp.)

EXAMPLES 1 TO 19, COMPARATIVE EXAMPLES 1 TO 3

Example 1

A polymerization vessel equipped with a stirrer, a reflux condenser, a thermometer, a nitrogen inlet tube, and a dropping funnel was charged with 280.7 parts of deionized water. Then, the internal temperature was increased to 75° C. under stirring and nitrogen flow. The dropping funnel was charged with a monomer emulsion including 520 parts of methyl methacrylate, 130 parts of 2-ethylhexyl acrylate, 340 parts of butyl acrylate, 10.0 parts of acrylic acid, 2.0 parts of t-dodecyl mercaptan (also referred to as t-DM) as a polymerization chain transfer agent, 180.0 parts of the polyoxyethylene alkyl ether-sulfosuccinate-disodium salt (i)-<1> preliminarily adjusted to a 20% aqueous solution, and 183.0 parts of deionized water. While the internal temperature of the polymerization vessel was maintained at 75° C., 27.0 parts of the monomer emulsion, and 5 parts of a 5% potassium persulfate aqueous solution and 10 parts of a 2% sodium hydrogen sulfite aqueous solution as polymerization initiators (oxidants) were added to initiate initial polymerization. After 40 minutes, the rest of the monomer emulsion was uniformly added dropwise over 210 minutes with the reaction system being maintained at 80° C. Simultaneously, 95 parts of a 5% potassium persulfate aqueous solution and 90 parts of a 2% sodium hydrogen sulfite aqueous solution were uniformly added dropwise over 210 minutes. After the completion of the dropwise addition, the temperature was maintained for 60 minutes to complete the polymerization.

The resulting reaction solution was cooled to room temperature, and 16.7 parts of 2-dimethylethanolamine and 39 parts of deionized water were added to give an acrylic emulsion (resin composition 1) having a nonvolatile content of 55.0%, a pH of 8.0, a viscosity of 190 mPa·s, an average particle size of 250 nm, and a weight average molecular weight of 103,000.

Example 2

An acrylic emulsion (resin composition 2) was prepared as in Example 1, except that 520 parts of styrene was used instead of 520 parts of methyl methacrylate in the monomer emulsion of Example 1. The acrylic emulsion had a nonvolatile content of 55.1%, a pH of 7.8, a viscosity of 100 mPa·s, an average particle size of 230 nm, and a weight average molecular weight of 90,000.

Example 3

An acrylic emulsion (resin composition 3) was prepared as in Example 1, except that the amount of the polyoxyethylene alkyl ether-sulfosuccinate-disodium salt (i)-<1> preliminarily adjusted to a 20% aqueous solution was changed from 180.0 parts to 100.0 parts in the monomer emulsion of Example 1. The acrylic emulsion had a nonvolatile content of 55.0%, a pH of 8.1, a viscosity of 120 mPa·s, an average particle size of 260 nm, and a weight average molecular weight of 102,000.

Example 4

An acrylic emulsion (resin composition 4) was prepared by adding 100.0 parts of a polyoxyethylene alkyl ether-sulfosuccinate-disodium salt (i)-<1> preliminarily adjusted to a 20% aqueous solution to an emulsion prepared by the same polymerization method as in Example 1. The acrylic emulsion had a nonvolatile content of 53.2% by mass, a pH of 8.0, a viscosity of 130 mPa·s, an average particle size of 255 nm, and a weight average molecular weight of 104,500.

Example 5

A polymerization vessel equipped with a stirrer, a reflux condenser, a thermometer, a nitrogen inlet tube, and a dropping funnel was charged with 280.7 parts of deionized water. Then, the internal temperature was increased to 75° C. under stirring and nitrogen flow. The dropping funnel was charged with a monomer emulsion including 520 parts of methyl methacrylate, 130 parts of 2-ethylhexyl acrylate, 340 parts of butyl acrylate, 10.0 parts of acrylic acid, 2.0 parts of t-DM as a polymerization chain transfer agent, 55 parts of the polyoxyethylene alkyl ether-sulfosuccinate-disodium salt (i)-<1> preliminarily adjusted to a 20% aqueous solution, 125 parts of the polyoxyethylene alkyl ether-sulfosuccinate-disodium salt (i)-<2> preliminarily adjusted to a 20% aqueous solution, and 183.0 parts of deionized water. While the internal temperature of the polymerization vessel was maintained at 75° C., 27.0 parts of the monomer emulsion, and 5 parts of a 5% potassium persulfate aqueous solution and 10 parts of a 2% sodium hydrogen sulfite aqueous solution as polymerization initiators (oxidants) were added to initiate initial polymerization. After 40 minutes, the rest of the monomer emulsion was uniformly added dropwise over 210 minutes with the reaction system being maintained at 80° C. Simultaneously, 95 parts of a 5% potassium persulfate aqueous solution and 90 parts of a 2% sodium hydrogen sulfite aqueous solution were uniformly added dropwise over 210 minutes. After the completion of the dropwise addition, the temperature was maintained for 60 minutes to complete the polymerization.

The resulting reaction solution was cooled to room temperature, and 16.7 parts of 2-dimethylethanolamine and 39 parts of deionized water were added to give an acrylic emulsion (resin composition 5) having a nonvolatile content of 55.2%, a pH of 8.0, a viscosity of 250 mPa·s, an average particle size of 225 nm, and a weight average molecular weight of 98,000.

Example 6

An acrylic emulsion (resin composition 6) was prepared as in Example 1, except that 180.0 parts of the polyoxyethylene alkyl ether-sulfosuccinic acid half ester salt (iii)-<1> preliminarily adjusted to a 20% aqueous solution was used instead of 180.0 parts of the polyoxyethylene alkyl ether-sulfosuccinate-disodium salt (i)-<1> preliminarily adjusted to a 20% aqueous solution in the monomer emulsion of Example 1. The acrylic emulsion had a nonvolatile content of 55.0%, a pH of 8.1, a viscosity of 230 mPa·s, an average particle size of 240 nm, and a weight average molecular weight of 101,000.

Example 7

An acrylic emulsion (resin composition 7) was prepared as in Example 1, except that 180.0 parts of the polyoxyethylene alkyl ether-sulfosuccinic acid half ester salt (iii)-<1> preliminarily adjusted to a 20% aqueous solution was used instead of 180.0 parts of the polyoxyethylene alkyl ether-sulfosuccinate-disodium salt (i)-<1> preliminarily adjusted to a 20% aqueous solution and the amount of t-DM was changed from 2.0 parts to 1.0 part in the monomer emulsion of Example 1. The acrylic emulsion had a nonvolatile content of 55.0%, a pH of 8.1, a viscosity of 210 mPa·s, an average particle size of 250 nm, and a weight average molecular weight of 415,000.

Example 8

An acrylic emulsion (resin composition 8) was prepared as in Example 1, except that 180.0 parts of the polyoxyethylene alkyl ether-sulfosuccinic acid half ester salt (iii)-<1> preliminarily adjusted to a 20% aqueous solution was used instead of 180.0 parts of the polyoxyethylene alkyl ether-sulfosuccinate-disodium salt (i)-<1> preliminarily adjusted to a 20% aqueous solution and the amount of t-DM was changed from 2.0 parts to 5.0 parts in the monomer emulsion of Example 1. The acrylic emulsion had a nonvolatile content of 55.0%, a pH of 8.1, a viscosity of 200 mPa·s, an average particle size of 270 nm, and a weight average molecular weight of 37,000.

Example 9

An acrylic emulsion (resin composition 9) was prepared as in Example 1, except that 130.0 parts of the polyoxyethylene alkyl ether-sulfosuccinic acid half ester salt (iii)-<1> preliminarily adjusted to a 20% aqueous solution and 50.0 parts of the polyoxyethylene alkyl ether-sulfosuccinic acid half ester salt (iii)-<2> preliminarily adjusted to a 20% aqueous solution were used instead of 180.0 parts of the polyoxyethylene alkyl ether-sulfosuccinate-disodium salt (i)-<1> preliminarily adjusted to a 20% aqueous solution in the monomer emulsion of Example 1. The acrylic emulsion had a nonvolatile content of 55.1%, a pH of 8.1, a viscosity of 180 mPa·s, an average particle size of 270 nm, and a weight average molecular weight of 105,500.

Example 10

An acrylic emulsion (resin composition 10) was prepared by mixing 100.0 parts of the polyoxyethylene alkyl ether-sulfosuccinate-disodium salt (i)-<2> preliminarily adjusted to a 20% aqueous solution with an emulsion prepared by the same polymerization method as in Example 1, except that 180.0 parts of the polyoxyethylene alkyl ether-sulfosuccinic acid half ester salt (iii)-<1> preliminarily adjusted to a 20% aqueous solution was used instead of 180.0 parts of the polyoxyethylene alkyl ether-sulfosuccinate-disodium salt (i)-<1> preliminarily adjusted to a 20% aqueous solution in the monomer emulsion of Example 1. The acrylic emulsion had a nonvolatile content of 53.3%, a pH of 8.2, a viscosity of 110 mPa·s, an average particle size of 265 nm, and a weight average molecular weight of 104,400.

Example 11

An acrylic emulsion (resin composition 11) was prepared as in Example 1, except that 100.0 parts of the N-alkyl monoamide disodium sulfosuccinate (iv) preliminarily adjusted to a 20% aqueous solution was used instead of 180.0 parts of the polyoxyethylene alkyl ether-sulfosuccinate-disodium salt (i)-<1> preliminarily adjusted to a 20% aqueous solution in the monomer emulsion of Example 1. The acrylic emulsion had a nonvolatile content of 55.0%, a pH of 8.3, a viscosity of 320 mPa·s, an average particle size of 235 nm, and a weight average molecular weight of 97,000.

Example 12

An acrylic emulsion (resin composition 12) was prepared as in Example 1, except that 50.0 parts of the dialkyl succinate sodium sulfonate salt (ii) preliminarily adjusted to a 20% aqueous solution and 50.0 parts of the N-alkyl monoamide disodium sulfosuccinate (iv) preliminarily adjusted to a 20% aqueous solution were used instead of 180.0 parts of the polyoxyethylene alkyl ether-sulfosuccinate-disodium salt (i)-<1> preliminarily adjusted to a 20% aqueous solution in the monomer emulsion of Example 1. The acrylic emulsion had a nonvolatile content of 55.0%, a pH of 8.0, a viscosity of 150 mPa·s, an average particle size of 260 nm, and a weight average molecular weight of 109,000.

Example 13

An acrylic emulsion (resin composition 13) was prepared as in Example 1, except that 180.0 parts of the sulfosuccinate-type reactive anionic surfactant (v) preliminarily adjusted to a 20% aqueous solution was used instead of 180.0 parts of the polyoxyethylene alkyl ether-sulfosuccinate-disodium salt (i)-<1> preliminarily adjusted to a 20% aqueous solution in the monomer emulsion of Example 1. The acrylic emulsion had a nonvolatile content of 53.5%, a pH of 8.2, a viscosity of 350 mPa·s, an average particle size of 220 nm, and a weight average molecular weight of 110,000.

Example 14

An acrylic emulsion (resin composition 14) was prepared as in Example 1, except that 180.0 parts of the N-alkyl monoamide disodium sulfosuccinate (iv) preliminarily adjusted to a 20% aqueous solution was used instead of 180.0 parts of the polyoxyethylene alkyl ether-sulfosuccinate-disodium salt (i)-<1> preliminarily adjusted to a 20% aqueous solution in the monomer emulsion of Example 1. The acrylic emulsion had a nonvolatile content of 54.5%, a pH of 8.0, a viscosity of 300 mPa·s, an average particle size of 205 nm, and a weight average molecular weight of 95,000.

Example 15

An acrylic emulsion (resin composition 15) was prepared as in Example 1, except that the amount of the methyl methacrylate was changed from 520 parts to 525 parts, the amount of the acrylic acid was changed from 10.0 parts to 5.0 parts, and the amount of t-DM was changed from 2.0 parts to 1.0 part in the monomer emulsion of Example 1. The acrylic emulsion had a nonvolatile content of 55.1%, a pH of 8.2, a viscosity of 200 mPa·s, an average particle size of 250 nm, and a weight average molecular weight of 253,000.

Example 16

An acrylic emulsion (resin composition 16) was prepared as in Example 1, except that 130.0 parts of the N-alkyl monoamide disodium sulfosuccinate (iv) preliminarily adjusted to a 20% aqueous solution and 50.0 parts of NEWCOL 707SF (trade name, polyoxyethylene polycyclic phenyl ether-sulfate, produced by Nippon Nyukazai Co., Ltd.) preliminarily adjusted to a 20% aqueous solution were used instead of 180.0 parts of the polyoxyethylene alkyl ether-sulfosuccinate-disodium salt (i)-<1> preliminarily adjusted to a 20% aqueous solution in the monomer emulsion of Example 1. The acrylic emulsion had a nonvolatile content of 55.1%, a pH of 8.3, a viscosity of 220 mPa·s, an average particle size of 260 nm, and a weight average molecular weight of 106,000.

Example 17

An acrylic emulsion (resin composition 17) was prepared as in Example 1, except that 100.0 parts of the polyoxyethylene alkyl ether-sulfosuccinate-disodium salt (i)-<1> preliminarily adjusted to a 20% aqueous solution and 80.0 parts of NEWCOL 707SF (trade name, polyoxyethylene polycyclic phenyl ether-sulfate, produced by Nippon Nyukazai Co., Ltd.) preliminarily adjusted to a 20% aqueous solution were used instead of 180.0 parts of the polyoxyethylene alkyl ether-sulfosuccinate-disodium salt (i)-<1> preliminarily adjusted to a 20% aqueous solution in the monomer emulsion of Example 1. The acrylic emulsion had a nonvolatile content of 55.3%, a pH of 8.3, a viscosity of 300 mPa·s, an average particle size of 210 nm, and a weight average molecular weight of 110,000.

Example 18

An acrylic emulsion (resin composition 18) was prepared as in Example 1, except that 50.0 parts of the N-alkyl monoamide disodium sulfosuccinate (iv) preliminarily adjusted to a 20% aqueous solution and 130.0 parts of NEWCOL 707SF (trade name, polyoxyethylene polycyclic phenyl ether-sulfate, produced by Nippon Nyukazai Co., Ltd.) preliminarily adjusted to a 20% aqueous solution were used instead of 180.0 parts of the polyoxyethylene alkyl ether-sulfosuccinate-disodium salt (i)-<1> preliminarily adjusted to a 20% aqueous solution in the monomer emulsion of Example 1. The acrylic emulsion had a nonvolatile content of 55.0%, a pH of 8.0, a viscosity of 350 mPa·s, an average particle size of 200 nm, and a weight average molecular weight of 105,000.

Example 19

An acrylic emulsion (resin composition 19) was prepared by mixing 100.0 parts of the polyoxyethylene alkyl ethersulfosuccinate-disodium salt (i)-<1> preliminarily adjusted to a 20% aqueous solution with an emulsion prepared by the same polymerization method as in Example 1, except that 180.0 parts of LEVENOL WX (trade name, sodium polyoxyethylene alkyl ether sulfate, produced by Kao Corporation) preliminarily adjusted to a 20% aqueous solution was used instead of 180.0 parts of the polyoxyethylene alkyl ether-sulfosuccinate-disodium salt (i)-<1> preliminarily adjusted to a 20% aqueous solution in the monomer emulsion of Example 1. The acrylic emulsion had a nonvolatile content of 53.1%, a pH of 7.9, a viscosity of 400 mPa·s, an average particle size of 200 nm, and a weight average molecular weight of 104,000.

Comparative Example 1

An acrylic emulsion (resin composition 20) was prepared as in Example 1, except that 180.0 parts of NEWCOL 707SF (trade name, polyoxyethylene polycyclic phenyl ether-sulfate, produced by Nippon Nyukazai Co., Ltd.) preliminarily adjusted to a 20% aqueous solution was used instead of 180.0 parts of the polyoxyethylene alkyl ether-sulfosuccinate-disodium salt (i)-<1> preliminarily adjusted to a 20% aqueous solution in the monomer emulsion of Example 1. The acrylic emulsion had a nonvolatile content of 55.0%, a pH of 7.9, a viscosity of 320 mPa·s, an average particle size of 295 nm, and a weight average molecular weight of 96,000.

Comparative Example 2

An acrylic emulsion (resin composition 21) was prepared as in Example 1, except that 180.0 parts of LEVENOL WX (trade name, sodium polyoxyethylene alkyl ether sulfate, produced by Kao Corporation) preliminarily adjusted to a 20% aqueous solution was used instead of 180.0 parts of the polyoxyethylene alkyl ether-sulfosuccinate-disodium salt (i)-<1> preliminarily adjusted to a 20% aqueous solution in the monomer emulsion of Example 1. The acrylic emulsion had a nonvolatile content of 55.2%, a pH of 8.0, a viscosity of 380 mPa·s, an average particle size of 210 nm, and a weight average molecular weight of 101,000.

Comparative Example 3

An acrylic emulsion (resin composition 22) was prepared as in Example 1, except that 520 parts of styrene was used instead of 520 parts of the methyl methacrylate, and 180.0 parts of NEWCOL 707SF (trade name, polyoxyethylene polycyclic phenyl ether-sulfate, produced by Nippon Nyukazai Co., Ltd.) preliminarily adjusted to a 20% aqueous solution was used instead of 180.0 parts of the polyoxyethylene alkyl ether-sulfosuccinate-disodium salt (i)-<1> preliminarily adjusted to a 20% aqueous solution in the monomer emulsion of Example 1. The acrylic emulsion had a nonvolatile content of 55.1%, a pH of 7.8, a viscosity of 165 mPa·s, an average particle size of 225 nm, and a weight average molecular weight of 92,000.

In Example 2 and Comparative Example 3, the Tg of the acrylic emulsion was 3° C., and in the other examples and comparative examples, the Tg of the acrylic emulsion was 4° C. The amount of the compound having a sulfosuccinic acid (salt) structure based on 100% by mass of the entire anionic surfactant was 72% by mass in Example 16, 56% by mass in Example 17, 28% by mass in Example 18, 36% by mass in Example 19, 100% by mass in the other examples, and 0% by mass in Comparative Examples 1 to 3.

<Preparation 1 of Coating Material>

Coating materials were prepared according to the following formulation using the respective resin compositions 1 to 19 in Examples 1 to 19 and the resin compositions 20 to 22 in Comparative Examples 1 to 3. The properties were evaluated (evaluation of appearance of coat, damping test, and mechanical stability) as described below. The results are shown in Table 1.

Resin compositions 1 to 22: 350 parts
Calcium carbonate NN #200[*1]: 620 parts
Dispersant AQUALIC DL-40S[*2]: 6 parts
Thickener ACRYSET WR-650[*3]: 4 parts

*1: Filler produced by Nitto Funka Kogyo K.K.
*2: Polycarboxylic acid-based dispersant (active ingredient: 44%) produced by Nippon Shokubai Co., Ltd.
*3: Alkali-soluble acrylic thickener (active ingredient: 30%) produced by Nippon Shokubai Co., Ltd.

The following shows the methods for evaluating the properties.

<Evaluation of Appearance of Coat>

Each coating material was applied to a steel plate (trade name: SPCC-SD, 75 mm in width, 150 mm in length, 0.8 mm in thickness, produced by Nippon Testpanel Co., Ltd.) so as to have a thickness of 4 mm. The applied coating material was dried in a hot air dryer at 150° C. for 50 minutes. The surface condition of the resulting dry coat was evaluated using the following criteria. The heating in the hot air dryer caused foaming of the coating material.

Good: No defect was observed.
Average: Slight blisters and/or cracks of the coat were partly observed.
Fair: Blisters and/or cracks of the coat were partly observed.
Poor: Blisters, peelings, and/or cracks were observed throughout the coat.

<Damping Test>

Each coating material was applied to a cold rolled steel plate (trade name: SPCC, 15 mm in width, 250 mm in length, 1.5 mm in thickness, produced by Nippon Testpanel Co., Ltd.) so as to have a thickness of 3 mm, and pre-dried at 80° C. for 30 minutes and then dried at 150° C. for 30 minutes. Thus, a damping coat with a surface density of 4.0 kg/m$^2$ was formed on the cold rolled steel plate. The heating in pre-drying and drying after pre-drying causes foaming of the coating material.

In the measurement of damping properties, the loss coefficients were evaluated at particular temperatures (20° C., 30° C., 40° C., 50° C., and 60° C.) by a cantilever method (loss coefficient measurement system produced by Ono Sokki Co., Ltd.). The damping properties were evaluated based on the total loss coefficient (the sum of the loss coefficients at 20° C., 30° C., 40° C., 50° C., and 60° C.). The larger the total loss coefficient, the better the damping properties.

<Evaluation of Mechanical Stability>

A 200-g portion of each of the resulting coating materials was put into a 500-ml polypropylene cup, and a 50 mm-diameter blade was attached at a height of 5 mm from the bottom of the cup. The coating material was stirred using a disperser at 2,000 rpm, and the time (minute) until the coating material turned into a gel was measured.

TABLE 1

|  |  |  | Ex. 1 | Ex. 2 | Ex. 3 | Ex. 4 | Ex. 5 | Ex. 6 | Ex. 7 | Ex. 8 | Ex. 9 | Ex. 10 | Ex. 11 |
|---|---|---|---|---|---|---|---|---|---|---|---|---|---|
|  | Resin composition |  | Resin compsn. 1 | Resin compsn. 2 | Resin compsn. 3 | Resin compsn. 4 | Resin compsn. 5 | Resin compsn. 6 | Resin compsn. 7 | Resin compsn. 8 | Resin compsn. 9 | Resin compsn. 10 | Resin compsn. 11 |
| Evaluation | Appearance |  | Good | Good | Good | Good | Average | Good | Average | Average | Good | Good | Good |
|  | Damping properties | 20° C. | 0.044 | 0.042 | 0.04 | 0.056 | 0.043 | 0.043 | 0.041 | 0.041 | 0.041 | 0.045 | 0.042 |
|  |  | 30° C. | 0.08 | 0.06 | 0.07 | 0.09 | 0.08 | 0.085 | 0.084 | 0.087 | 0.083 | 0.09 | 0.06 |
|  |  | 40° C. | 0.164 | 0.162 | 0.16 | 0.168 | 0.158 | 0.161 | 0.145 | 0.15 | 0.157 | 0.165 | 0.164 |
|  |  | 50° C. | 0.104 | 0.102 | 0.09 | 0.106 | 0.09 | 0.101 | 0.104 | 0.1 | 0.09 | 0.103 | 0.101 |
|  |  | 60° C. | 0.046 | 0.044 | 0.04 | 0.048 | 0.017 | 0.041 | 0.039 | 0.043 | 0.035 | 0.045 | 0.043 |
|  |  | Total | 0.438 | 0.41 | 0.4 | 0.468 | 0.388 | 0.431 | 0.413 | 0.421 | 0.406 | 0.448 | 0.41 |
|  | Mechanical stability (min) |  | 64 | 70 | 58 | 72 | 67 | 60 | 59 | 60 | 58 | 75 | 65 |

|  |  |  | Ex. 12 | Ex. 13 | Ex. 14 | Ex. 15 | Ex. 16 | Ex. 17 | Ex. 18 | Ex. 19 | Comp. Ex. 1 | Comp. Ex. 2 | Comp. Ex. 3 |
|---|---|---|---|---|---|---|---|---|---|---|---|---|---|
|  | Resin composition |  | Resin compsn. 12 | Resin compsn. 13 | Resin compsn. 14 | Resin compsn. 15 | Resin compsn. 16 | Resin compsn. 17 | Resin compsn. 18 | Resin compsn. 19 | Resin compsn. 20 | Resin compsn. 21 | Resin compsn. 22 |
| Evaluation | Appearance |  | Good | Fair | Good | Good | Good | Fair | Fair | Fair | Poor | Poor | Poor |
|  | Damping properties | 20° C. | 0.04 | 0.042 | 0.043 | 0.041 | 0.039 | 0.027 | 0.03 | 0.04 | 0.017 | 0.025 | 0.018 |
|  |  | 30° C. | 0.05 | 0.05 | 0.09 | 0.07 | 0.088 | 0.07 | 0.049 | 0.049 | 0.06 | 0.05 | 0.05 |
|  |  | 40° C. | 0.156 | 0.157 | 0.16 | 0.155 | 0.151 | 0.146 | 0.144 | 0.156 | 0.15 | 0.14 | 0.15 |
|  |  | 50° C. | 0.096 | 0.1 | 0.102 | 0.09 | 0.101 | 0.101 | 0.09 | 0.09 | 0.09 | 0.07 | 0.09 |
|  |  | 60° C. | 0.044 | 0.03 | 0.046 | 0.046 | 0.045 | 0.03 | 0.035 | 0.035 | 0.03 | 0.02 | 0.03 |
|  |  | Total | 0.386 | 0.379 | 0.441 | 0.402 | 0.424 | 0.374 | 0.348 | 0.37 | 0.347 | 0.305 | 0.338 |
|  | Mechanical stability (min) |  | 65 | 57 | 70 | 60 | 68 | 64 | 55 | 56 | 35 | 33 | 35 |

Comparison between Examples 1, 6, 13, and 14 and Comparative Examples 1 and 2, among which the conditions are the same other than the type of the damping-imparting agent put into the polymerization vessel, demonstrates that the damping properties, mechanical stability, and appearance are better in Examples 1, 6, 13, and 14 because a polyoxyethylene alkyl ether-sulfosuccinate-disodium salt having a sulfosuccinic acid salt structure is used as the damping-imparting agent in Example 1, a polyoxyethylene alkyl ether-sulfosuccinic acid half ester salt having a sulfosuccinic acid salt structure is used as the damping-imparting agent in Example 6, a reactive emulsifier having a sulfosuccinic acid salt structure is used as the damping-imparting agent in Example 13, and an N-alkyl monoamide disodium sulfosuccinate having a sulfosuccinic acid salt structure is used as the damping-imparting agent in Example 14. In particular, these effects are more significant in Examples 1, 6, and 14 in which the compound having a sulfosuccinic acid salt structure does not have a reactive unsaturated carbon-carbon bond. Similarly, comparison between Example 2 and Comparative Example 3 demonstrates that the damping properties, mechanical stability, and appearance are better in Example 2 because in Example 2, a polyoxyethylene alkyl ether-sulfosuccinate-disodium salt having a sulfosuccinic acid salt structure is used as the damping-imparting agent. Furthermore, comparison between Example 19 and Comparative Example 2 demonstrates that the damping properties, mechanical stability, and appearance are better in Example 19 because in Example 19, a polyoxyethylene alkyl ether-sulfosuccinate-disodium salt having a sulfosuccinic acid salt structure is added as an emulsifier after completion of the polymerization of the monomer component.

Among Examples 6 to 8, the conditions are the same other than the amount of the polymerization chain transfer agent (t-DM) put into a polymerization vessel. The polymer that forms the emulsion obtained in Example 6 has a weight average molecular weight of 101,000, the polymer that forms the emulsion obtained in Example 7 has a weight average molecular weight of 415,000, and the polymer that forms the emulsion obtained in Example 8 has a weight average molecular weight of 37,000. It is demonstrated that any of these emulsions of Examples 6 to 8 different in weight average molecular weight achieve better damping properties, mechanical stability, and appearance. The damping properties and appearance in Example 6 are particularly better.

Comparison between Example 17 and Comparative Example 1, between which the conditions are the same other than the type of the damping-imparting agent put into a polymerization vessel, demonstrates that the damping properties, mechanical stability, and appearance in Example 17 are better than those in Comparative Example 1, and Example 17 achieves the effects of the present invention because in Comparative Example 1, only a polyoxyethylene polycyclic phenyl ether-sulfate is used as the damping-imparting agent, but in Example 17, a polyoxyethylene polycyclic phenyl ether-sulfate and a polyoxyethylene alkyl ether-sulfosuccinate-disodium salt having a sulfosuccinic acid salt structure are used in combination and the proportion of the polyoxyethylene alkyl ether-sulfosuccinate-disodium salt in the entire anionic surfactant is 56% by mass.

As described above, comparison between the examples and the corresponding comparative examples demonstrates that the damping properties, mechanical stability, and appearance in the examples are better than those in the comparative examples because in the examples, a compound having a sulfosuccinic acid salt structure is used in the coating material as an emulsifier which is used for a monomer component or after completion of the polymerization of a monomer component, but in the comparative examples, no component having a sulfosuccinic acid salt structure is used in the coating material. Such effects are considered to be imparted also by a component having a sulfosuccinic acid (salt) structure with a similar chemical structure. Therefore, it is apparent that based on the results of the examples, the present invention can be applied to the full technical scope of the present invention and the various embodiments disclosed herein, and advantageous effects can be obtained.

Comparison between Example 1 and Example 3 demonstrates that the damping properties, mechanical stability, and the like in Example 1 are better than those in Example 3 because in Example 1, 180 parts of the compound having a sulfosuccinic acid salt structure preliminarily adjusted to a 20% aqueous solution is used as the damping-imparting agent, but in Example 3, 100 parts of the compound having a sulfosuccinic acid salt structure preliminarily adjusted to a 20% aqueous solution is used.

Furthermore, comparison between Example 1 and Example 4, both of which include the same step of polymerizing a monomer component, demonstrates that the damping properties and mechanical stability are better in Example 4 because in Example 4, a compound having a sulfosuccinic acid salt structure is further added as the damping-imparting agent after completion of the polymerization step. Similarly, comparison between Example 6 and Example 10, both of which include the same step of polymerizing a monomer component, demonstrates that the damping properties and mechanical stability are better in Example 10 because in Example 10, a compound having a sulfosuccinic acid salt structure is added as the damping-imparting agent after completion of the polymerization step.

In particular, it is demonstrated that the damping properties are remarkably improved in Example 4 in which a compound having a sulfosuccinic acid salt structure with an average number of moles of oxyethylene groups added of 8 is added after completion of the polymerization step.

Comparison between Example 1 and Example 5 demonstrates that, in Example 1 in which a compound having a sulfosuccinic acid salt structure with an average number of moles of oxyethylene groups added of 8 is used, the mechanical stability and appearance are sufficiently excellent and also the damping properties are much better than that in Example 5 in which the compound is used in combination with a compound having a sulfosuccinic acid salt structure with an average number of moles of oxyethylene groups added of 2. Similarly, comparison between Example 6 and Example 9 demonstrates that, in Example 6 in which a compound having a sulfosuccinic acid salt structure with an average number of moles of oxyethylene groups added of 9 is used, the mechanical stability and appearance are sufficiently excellent and also the damping properties are much better than that in Example 9 in which the compound is used in combination with a compound having a sulfosuccinic acid salt structure with an average number of moles of oxyethylene groups added of 3.

The proportions of the compound having a sulfosuccinic acid (salt) structure in the entire anionic surfactant in Examples 14, 16, and 18 are 100%, 72%, and 28%, respectively. It is demonstrated that the damping properties, mechanical stability, and appearance are excellent in Examples 14, 16, and 18. In particular, the damping properties, mechanical stability, and appearance in Examples 14 and 16 are better, and the damping properties and mechanical stability in Example 14 are particularly better.

EXAMPLES 20 TO 25, COMPARATIVE EXAMPLES 4 TO 7

Example 20

A polymerization vessel equipped with a stirrer, a reflux condenser, a thermometer, a nitrogen inlet tube, and a dropping funnel was charged with 350.6 parts of deionized water. Then, the internal temperature was increased to 75° C. under stirring and nitrogen flow. The dropping funnel was charged with a monomer emulsion including 520 parts of methyl methacrylate, 130 parts of 2-ethylhexyl acrylate, 340 parts of butyl acrylate, 10.0 parts of acrylic acid, 2.0 parts of t-DM, 75.0 parts of the polyoxyethylene alkyl ether-sulfosuccinate-disodium salt (i)-<1> preliminarily adjusted to a 20% aqueous solution, and 230.0 parts of deionized water. While the internal temperature of the polymerization vessel was maintained at 75° C., 27.0 parts of the monomer emulsion, and 5 parts of a 5% potassium persulfate aqueous solution and 10 parts of a 2% sodium hydrogen sulfite aqueous solution as polymerization initiators (oxidants) were added to initiate initial polymerization. After 40 minutes, the rest of the monomer emulsion was uniformly added dropwise over 210 minutes with the reaction system being maintained at 80° C. Simultaneously, 95 parts of a 5% potassium persulfate aqueous solution and 90 parts of a 2% sodium hydrogen sulfite aqueous solution were uniformly added dropwise over 210 minutes. After the completion of the dropwise addition, the temperature was maintained for 60 minutes to complete the polymerization.

The resulting reaction solution was cooled to room temperature, and 16.7 parts of 2-dimethylethanolamine and an appropriate amount of deionized water were added to give an acrylic emulsion (resin composition 23) having a nonvolatile content of 55.0%, a pH of 7.8, a viscosity of 300 mPa·s, an average particle size of 240 nm, and a weight average molecular weight of 103,000.

Example 21

An acrylic emulsion (resin composition 24) was prepared as in Example 20, except that the amount of the polyoxyethylene alkyl ether-sulfosuccinate-disodium salt (i)-<1> preliminarily adjusted to a 20% aqueous solution was changed from 75.0 parts to 150 parts in the monomer emulsion of Example 20. The acrylic emulsion had a nonvolatile content of 55.1%, a pH of 7.8, a viscosity of 450 mPa·s, an average particle size of 190 nm, and a weight average molecular weight of 95,000.

Example 22

An acrylic emulsion (resin composition 25) was prepared as in Example 20, except that 75.0 parts of the polyoxyethylene alkyl ether-sulfosuccinic acid half ester salt (iii)-<1> preliminarily adjusted to a 20% aqueous solution was used instead of 75.0 parts of the polyoxyethylene alkyl ether-sulfosuccinate-disodium salt (i)-<1> preliminarily adjusted to a 20% aqueous solution in the monomer emulsion of Example 20. The acrylic emulsion had a nonvolatile content of 55.0%, a pH of 8.1, a viscosity of 200 mPa·s, an average particle size of 260 nm, and a weight average molecular weight of 110,000.

Example 23

An acrylic emulsion (resin composition 26) was prepared as in Example 22, except that the amount of the polyoxyethylene alkyl ether-sulfosuccinic acid half ester salt (iii)-<1> preliminarily adjusted to a 20% aqueous solution was changed from 75.0 parts to 150 parts in the monomer emulsion of Example 22. The acrylic emulsion had a nonvolatile content of 55.0%, a pH of 8.0, a viscosity of 350 mPa·s, an average particle size of 210 nm, and a weight average molecular weight of 103,000.

Example 24

An acrylic emulsion (resin composition 27) was prepared as in Example 20, except that 75.0 parts of the N-alkyl monoamide disodium sulfosuccinate (iv) preliminarily adjusted to a 20% aqueous solution was used instead of 75.0 parts of the polyoxyethylene alkyl ether-sulfosuccinate-disodium salt (i)-<1> preliminarily adjusted to a 20% aqueous solution in the monomer emulsion of Example 20. The acrylic emulsion had a nonvolatile content of 55.1%, a pH of 8.0, a viscosity of 250 mPa·s, an average particle size of 220 nm, and a weight average molecular weight of 98,000.

Example 25

An acrylic emulsion (resin composition 28) was prepared as in Example 24, except that the amount of the N-alkyl monoamide disodium sulfosuccinate (iv) preliminarily adjusted to a 20% aqueous solution was changed from 75.0 parts to 150 parts in the monomer emulsion of Example 24. The acrylic emulsion had a nonvolatile content of 55.1%, a pH of 8.1, a viscosity of 400 mPa·s, an average particle size of 170 nm, and a weight average molecular weight of 105,000.

Comparative Example 4

An acrylic emulsion (resin composition 29) was prepared as in Example 20, except that 75.0 parts of NEWCOL 707SF (trade name, polyoxyethylene polycyclic phenyl ether-sulfate, produced by Nippon Nyukazai Co., Ltd.) preliminarily adjusted to a 20% aqueous solution was used instead of 75 parts of the polyoxyethylene alkyl ether-sulfosuccinate-disodium salt (i)-<1> preliminarily adjusted to a 20% aqueous solution in the monomer emulsion of Example 20. The acrylic emulsion had a nonvolatile content of 55.0%, a pH of 7.9, a viscosity of 400 mPa·s, an average particle size of 230 nm, and a weight average molecular weight of 111,000.

Comparative Example 5

An acrylic emulsion (resin composition 30) was prepared as in Comparative Example 4, except that the amount of NEWCOL 707SF (trade name, polyoxyethylene polycyclic phenyl ether-sulfate, produced by Nippon Nyukazai Co., Ltd.) preliminarily adjusted to a 20% aqueous solution was changed from 75.0 parts to 150 parts in the monomer emulsion of Comparative Example 4. The acrylic emulsion had a nonvolatile content of 55.0%, a pH of 7.9, a viscosity of 450 mPa·s, an average particle size of 190 nm, and a weight average molecular weight of 98,000.

Comparative Example 6

An acrylic emulsion (resin composition 31) was prepared as in Example 20, except that 75.0 parts of LEVENOL WX (trade name, sodium polyoxyethylene alkyl ether sulfate, produced by Kao Corporation) preliminarily adjusted to a 20% aqueous solution was used instead of 75.0 parts of the polyoxyethylene alkyl ether-sulfosuccinate-disodium salt (i)-<1> preliminarily adjusted to a 20% aqueous solution in the monomer emulsion of Example 20. The acrylic emulsion had a nonvolatile content of 55.2%, a pH of 8.0, a viscosity of 300 mPa·s, an average particle size of 250 nm, and a weight average molecular weight of 101,000.

Comparative Example 7

An acrylic emulsion (resin composition 32) was prepared as in Comparative Example 6, except that the amount of LEVENOL WX (trade name, sodium polyoxyethylene alkyl ether sulfate, produced by Kao Corporation) preliminarily adjusted to a 20% aqueous solution was changed from 75.0 parts to 150 parts in the monomer emulsion of Comparative Example 6. The acrylic emulsion had a nonvolatile content of 55.1%, a pH of 7.8, a viscosity of 350 mPa·s, an average particle size of 220 nm, and a weight average molecular weight of 109,000.

<Preparation 2 of Coating Material>

Coating materials were prepared according to the following formulation using the respective resin compositions 23 to 28 in Examples 20 to 25 and the resin compositions 29 to 32 in Comparative Examples 4 to 7. Then, the total loss coefficients of the coating materials were determined, and the damping increase rates were calculated as described below for the combination of Examples 20 and 21 in both of which the damping-imparting agent (i)-<1> was used, the combination of Examples 22 and 23 in both of which the damping-imparting agent (iii)-<1> was used, the combination of Examples 24 and 25 in both of which the damping-imparting agent (iv) was used, the combination of Comparative Examples 4 and 5 in both of which NEWCOL 707SF was used, and the combination of Comparative Examples 6 and 7 in both of which LEVENOL WX was used. The results are shown in Table 2.

Resin compositions 23 to 32: 350 parts
Calcium carbonate NN #200[*1]: 525 parts
Dispersant AQUALIC DL-40S[*2]: 6 parts
Thickener ACRYSET WR-650[*3]: 4 parts

*1: Filler produced by Nitto Funka Kogyo K.K.
*2: Polycarboxylic acid-based dispersant (active ingredient: 44%) produced by Nippon Shokubai Co., Ltd.
*3: Alkali-soluble acrylic thickener (active ingredient: 30%) produced by Nippon Shokubai Co., Ltd.

<Damping Increase Rate>

Each coating material was applied to a cold rolled steel plate (trade name: SPCC, 15 mm in width, 250 mm in length, 1.5 mm in thickness, produced by Nippon Testpanel Co., Ltd.) so as to have a thickness of 2 mm, and pre-dried at 80° C. for 30 minutes and then dried at 150° C. for 30 minutes. Thus, a damping coat with a surface density of 4.0 kg/m$^2$ was formed on the cold rolled steel plate. The heating in in pre-drying and drying after pre-drying caused foaming of the coating material.

In the measurement of damping properties, the loss coefficients were evaluated at particular temperatures (20° C., 30° C., 40° C., 50° C., and 60° C.) by a cantilever method (loss coefficient measurement system produced by Ono Sokki Co., Ltd.). The damping increase rates were evaluated based on the total loss coefficient (the sum of loss coefficients at 20° C., 30° C., 40° C., 50° C., and 60° C.), and were determined using the following expression:

$$\text{Damping increase rate (\%)} = \{(a-b)/b\} \times 100(\%)$$

wherein a is the total loss coefficient when the amount of the damping-imparting agent added is 3.0% and b is the total loss coefficient when the amount of the damping-imparting agent added is 1.5%.

TABLE 2

| Damping imparting agent | Total damping properties | | Damping increase rate |
|---|---|---|---|
| | Amount of agent 1.50% | Amount of agent 3.00% | |
| 20% (i)-<1> | 0.38 | 0.41 | 7.9% |
| 20% (iii)-<1> | 0.393 | 0.425 | 8.1% |
| 20% (iv) | 0.401 | 0.432 | 7.7% |
| 20% NEWCOL 707SF | 0.306 | 0.311 | 1.6% |
| 20% LEVENOL WX | 0.316 | 0.31 | −1.9% |

In light of Examples 20 to 25 and Comparative Examples 4 to 7 and the mechanism of action imparted by the constitution of the present invention described herein, the damping-imparting agent which contains a compound having a sulfosuccinic acid (salt) structure was found to greatly improve the damping properties of the coat.

The invention claimed is:

1. A resin composition for damping materials, comprising:
an emulsion comprising a (meth)acrylic polymer, the emulsion being prepared by polymerizing a monomer component comprising 0.1% to 3% by mass of (meth)acrylic acid monomer and 97% to 99.9% by mass of one or more other copolymerizable unsaturated monomers, the emulsion having a glass transition temperature from −20° C. to 40° C.;
an aqueous solvent in which the emulsion dispersed; and
a component having a sulfosuccinic acid (salt) structure and containing no reactive unsaturated carbon-carbon bond, the component having a sulfosuccinic acid (salt) structure being 70% or more by mass of all anionic surfactants in the resin composition, the component having a sulfosuccinic acid (salt) structure being represented by formula (1):

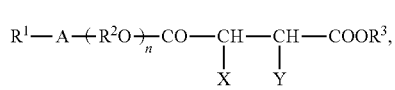

wherein $R^1$ is one of a hydrogen atom or a C1-C30 monovalent alkyl group,
$R^2$ is a C2-C4 alkylene group,
$R^3$ is one of a hydrogen atom, an alkyl group, a metal salt, an ammonium salt, or an organic amine salt,
-A- is one of —O— or —NH—,
X and Y are each respectively one of a hydrogen atom or a sulfonic acid (salt) group, and at least one of the X and the Y being the sulfonic acid (salt) group, and
n is either i) 3 to 200 or ii) 0 and the -A- is the —NH—, n being a molar average.

2. The resin composition for damping materials according to claim 1,
wherein the emulsion has a weight average molecular weight of 20,000 to 800,000.

3. The resin composition for damping materials according to claim 1,
wherein the resin composition contains the component having a sulfosuccinic acid (salt) structure in an amount of 0.1% to 20% by mass based on 100% by mass of the whole monomer component used as a material of the emulsion.

4. The resin composition for damping materials according to claim 1,
wherein the emulsion comprises a polymer that includes a carboxylic acid (salt) group-containing monomer unit.

5. A coating material comprising:
the resin composition for damping materials according to claim 1; and
a pigment.

6. The coating material according to claim 5,
wherein the amount of a thermally expandable encapsulated foaming agent is 2% by mass or less based on 100% by mass of the whole monomer component used as a material of the emulsion.

7. A coat obtained from the coating material according to claim 5.

8. A method for producing a coat, comprising:
heating a coating material that contains an emulsion prepared by polymerizing a monomer component, a component having a sulfosuccinic acid (salt) structure and containing no reactive unsaturated carbon-carbon bond, and a pigment to foam the coating material, thereby producing a coat, wherein
the emulsion comprises a (meth)acrylic polymer and has a glass transition temperature from −20° C. to 40° C., the monomer component comprising 0.1% to 3% by mass of (meth)acrylic acid monomer and 97% to 99.9% by mass of one or more other copolymerizable unsaturated monomers, and
the component having a sulfosuccinic acid (salt) structure being 70% or more by mass of all anionic surfactants in the coating material, and the component having a sulfosuccinic acid (salt) structure is represented by formula (1):

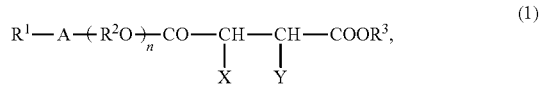

$R^1$ is one of a hydrogen atom or a C1-C30 monovalent alkyl group,
$R^2$ is a C2-C4 alkylene group,
$R^3$ is one of a hydrogen atom, an alkyl group, a metal salt, an ammonium salt, or an organic amine salt,
-A- is one of —O— or —NH—,
X and Y are each respectively one of a hydrogen atom or a sulfonic acid (salt) group, and at least one of the X and the Y being the sulfonic acid (salt) group, and
n is either i) 3 to 200 or ii) 0 and the -A- is the —NH—, n being a molar average.

9. The coating material according to claim 5,
wherein at least part of the component having a sulfosuccinic acid (salt) structure is contained as an emulsifier that forms the emulsion.

10. The resin composition for damping materials according to claim 1, wherein the amount of the component having a sulfosuccinic acid (salt) structure in the resin composition is 2% or more by mass based on 100% by mass of the whole monomer component used as a material of the emulsion.

11. The resin composition for damping materials according to claim 10, wherein the amount of the component having a sulfosuccinic acid (salt) structure in the resin composition is 3% or more by mass based on 100% by mass of the whole monomer component used as the material of the emulsion.

12. The resin composition for damping materials according to claim 1, wherein the n is 3 to 200, the $R^1$ is the C1-C30 monovalent alkyl group, and the $R^3$ is the alkyl group, or the n is 0 and the -A- is the —NH—.

\* \* \* \* \*